(12) United States Patent
Furukawa

(10) Patent No.: US 6,204,380 B1
(45) Date of Patent: Mar. 20, 2001

(54) PRODUCTION PYRIDAZINE HERBICIDES

(75) Inventor: Takashi Furukawa, Toyonaka (JP)

(73) Assignee: Sumitomo Chemical Company, Limited, Osaka-fu (JP)

(*) Notice: Subject to any disclaimer, the term of this patent is extended or adjusted under 35 U.S.C. 154(b) by 0 days.

(21) Appl. No.: 09/284,799

(22) PCT Filed: Oct. 16, 1997

(86) PCT No.: PCT/JP97/03727

§ 371 Date: Apr. 21, 1999

§ 102(e) Date: Apr. 21, 1999

(87) PCT Pub. No.: WO98/17633

PCT Pub. Date: Apr. 30, 1998

(30) Foreign Application Priority Data

Oct. 21, 1996 (JP) .................................................. 8-278256

(51) Int. Cl.$^7$ .................................................. C07C 251/76

(52) U.S. Cl. ........................... 544/52; 544/105; 548/165; 548/170; 548/221; 548/259; 548/260; 548/261; 549/55; 549/466; 560/34

(58) Field of Search ................................ 560/34; 549/55; 549/466; 548/165, 170, 221, 259, 260, 261; 544/52, 105

(56) References Cited

FOREIGN PATENT DOCUMENTS

| 0143281 | 6/1985 | (EP) . |
| 97 07104 | 2/1997 | (WO) . |

OTHER PUBLICATIONS

B.D. Schober et al., J. Heterocycl. Chem. (JHTCAD, 0022152X); 1989 vol. 26 (1); pp. 169–176, Karl–Frazens–Univ. Graz;Inst. Org. Chem,; Graz; A–8010; Austria (AT), XP002051833.

Chemical Abstracts, vol. 60, No. 5, Mar. 2, 1964 Columbus, Ohio US; abstract No. 5436e, E.M. Rokhlin column 5436; XP002051834.

Chemical Abstracts, vol. 51, No. 4, 1956 Columbus, Ohio, US; abstract No. 9643, R.B. Bradbury, column 9643; XP002051835.

Primary Examiner—Mukund J. Shah
Assistant Examiner—Deepak R. Rao
(74) Attorney, Agent, or Firm—Birch, Stewart, Kolasch & Birch, LLP

(57) ABSTRACT

Carboxylic acid ester derivatives of formula (1):

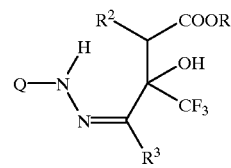

wherein R is $C_1$–$C_6$ alkyl, $R^2$ and $R^3$ are independently hydrogen or $C_1$–$C_3$ alkyl, and Q is optionally substituted phenyl, can be easily converted by ring closing into pyridazin-3-one derivatives of formula (7):

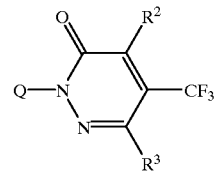

The carboxylic acids of formula (1) can be produced by reacting hydrazone compounds of formula (5):

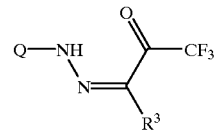

wherein $R^3$ and Q are as defined above, with malonic acid monoester derivatives of formula (6):

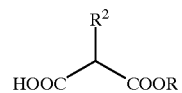

wherein R and $R^2$ are as defined above, in the presence of a base.

10 Claims, No Drawings

PRODUCTION PYRIDAZINE HERBICIDES

This application is a national phase under 35 U.S.C. §371 of PCT International Application No. PCT/JP97/03727 which has an International filing date of Oct. 16, 1997 which designated the United States of America.

1. Technical Field

The present invention relates to the production of pyridazine herbicides, and more particularly, it relates to carboxylic acid ester derivatives useful as intermediates for the production of pyridazin-3-one derivatives, a process for producing these intermediates, and a process for producing pyridazin-3-one derivatives from these intermediates.

2. Background Art

Pyridazin-3-one derivatives of formula (7):

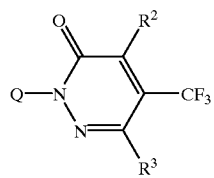

wherein $R^2$ and $R^3$ are independently hydrogen or $C_1$–$C_3$ alkyl, and Q is optionally substituted phenyl, have excellent herbicidal activity, including the following examples:

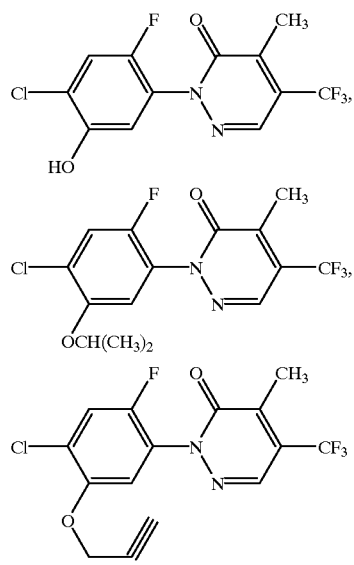

The production of pyridazin-3-one derivatives in a favorable manner is preferred for the development of pyridazine herbicides with excellent activity.

DISCLOSURE OF INVENTION

The present inventors have intensively studied to find a process for producing pyridazin-3-one derivatives in a favorable manner. As a result, they have found that carboxylic acid esters of formula (1):

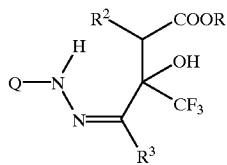

wherein R is $C_1$–$C_6$ alkyl, and $R^2$, $R^3$ and Q are as defined above, can be easily converted into pyridazin-3-one derivatives of formula (7) and therefore serve as their important intermediates, thereby completing the present invention.

Thus, the present invention provides compounds of formula (1):

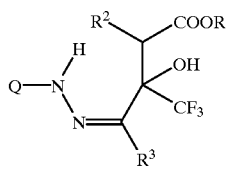

wherein R is $C_1$–$C_6$ alkyl, and $R^2$, $R^3$ and Q are as defined above, which compounds are hereinafter referred to as the present compound(s), a process for their production, and a process for producing pyridazin-3-one derivatives of formula (7):

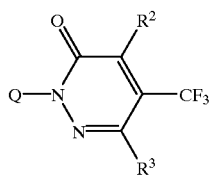

wherein $R^2$, $R^3$ and Q are as defined above, comprising ring closing the compounds of formula (1).

Examples of the optionally substituted phenyl group represented by Q may include, for example, groups Q-1, Q-2, Q-3, Q-4 and Q-5 of formula (2):

Q-1

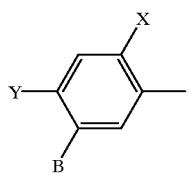

Q-2

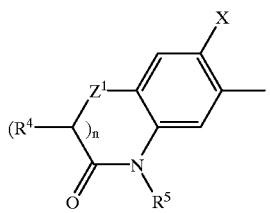

-continued

Q-3

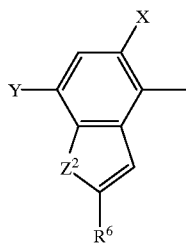

Q-4

Q-5 wherein X is hydrogen or halogen;
Y is halogen, nitro, cyano or trifluoromethyl;
$Z^1$ and $Z^2$ are independently oxygen or sulfur;
n is 0 or 1;
$R^4$ is hydrogen or $C_1$–$C_3$ alkyl;
$R^5$ is $C_1$–$C_6$ alkyl, $C_1$–$C_6$ haloalkyl, ($C_3$–$C_6$ cycloalkyl) $C_1$–$C_6$ alkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_3$ alkoxy $C_1$–$C_3$ alkoxy $C_1$–$C_3$ alkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbony $C_1$–$C_6$ alkyl, ($C_3$–$C_8$ cycloalkoxy) carbonyl $C_1$–$C_6$ alkyl, —$CH_2CON(R^{12})R^{13}$, —$CH_2COON(R^{12})R^{13}$, $CH(C_1$–$C_4$ alkyl)CON($R^{12}$) $R^{13}$, —$CH(C_1$–$C_4$ alkyl)COON($R^{12}$)$R^{13}$, $C_1$–$C_4$ alkylthio $C_1$–$C_4$ alkyl or hydroxy $C_1$–$C_6$ alkyl;
$R^{12}$ and $R^{13}$ are independently hydrogen, $C_1$–$C_6$ alkyl, $C_3$–$C_8$ cycloalkyl, $C_1$–$C_6$ haloalkyl, $C_3$–$C_6$ alkenyl, $C_3$–$C_6$ alkynyl, cyano $C_1$–$C_6$ alkyl, $C_1$–$C_3$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl, ($C_1$–$C_6$ alkyl)carbonyloxy $C_2$–$C_6$ alkyl, ($C_1$–$C_6$ alkyl) carbonylamino $C_2$–$C_6$ alkyl, hydroxy $C_2$–$C_6$ alkyl, optionally substituted benzyl, optionally substituted phenyl or {($C_1$–$C_4$ alkoxy) $C_1$–$C_4$ alkyl}carbonyl $C_1$–$C_6$ alkyl, or $R^{12}$ and $R^{13}$ are taken together to form trimethylene, tetramethylene, penta-methylene, ethyleneoxyethylene or ethylenethioethylene;
$R^6$ is $C_1$–$C_6$ alkyl, $C_1$–$C_6$ haloalkyl, cyano, carboxyl, hydroxy $C_1$–$C_6$ alkyl, $C_1$–$C_6$ alkoxy $C_1$–$C_6$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl or ($C_1$–$C_6$ alkoxy)carbonyl;
$R^7$ is hydrogen or $C_1$–$C_6$ alkyl;
$R^8$ is $C_1$–$C_6$ alkyl, $C_1$–$C_6$ haloalkyl, hydroxy $C_1$–$C_6$ alkyl, $C_1$–$C_4$ alkoxy $C_1$–$C_4$ alkyl, $C_1$–$C_3$ alkoxy $C_1$–$C_3$ alkoxy $C_1$–$C_3$ alkyl, ($C_1$–$C_6$ alkyl)carbonyloxy $C_1$–$C_6$ alkyl, ($C_1$–$C_6$ haloalkyl)carbonyl $C_1$–$C_6$ alkyl, carboxyl, carboxy $C_1$–$C_6$ alkyl, ($C_1$–$C_8$ alkoxy) carbonyl, ($C_1$–$C_6$ haloalkoxy)carbonyl, ($C_3$–$C_{10}$ cycloalkoxy)carbonyl, ($C_3$–$C_8$ alkenyloxy)carbonyl, ($C_3$–$C_8$ alkynyloxy)carbonyl, ($C_1$–$C_6$ alkyl) aminocarbonyl, di($C_1$–$C_6$ alkyl)aminocarbonyl, ($C_1$–$C_6$ alkyl)aminocarbonyloxy $C_1$–$C_6$ alkyl or di($C_1$–$C_6$ alkyl)aminocarbonyloxy $C_1$–$C_6$ alkyl;
B is hydrogen, halogen, nitro, cyano, chlorosulfonyl, $OR^1$, $SR^1$, $SO_2OR^{21}$, $COOR^{22}$, $CR^{23}$=$CR^{24}COOR^{25}$ or $CH_2CHWCOOR^{25}$;
W is hydrogen, chlorine or bromine;
$R^1$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alky ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_3$–$C_8$ cycloalkyl) $C_1$–$C_6$ alkoxycarbonyl $C_1$–$C_6$ alkyl, —$CH_2COON(R^{12})R^{13}$, —$CH(C_1$–$C_4$ alkyl)COON ($R^{12})R^{13}$, —$CH_2CON(R^{12})R^{13}$, —$CH(C_1$–$C_4$ alkyl) CON($R^{12})R^{13}$, $C_2$–$C_6$ alkenyloxycarbonyl $C_1$–$C_6$ alkyl, $C_3$–$C_6$ haloalkenyloxycarbonyl $C_1$–$C_6$ alkyl, $C_3$–$C_6$ alkynyloxycarbonyl $C_1$–$C_6$ alkyl, $C_3$–$C_6$ haloalkynyloxycarbonyl $C_1$–$C_6$ alkyl, ($C_1$–$C_6$ alkylthio)carbonyl $C_1$–$C_6$ alkyl, ($C_1$–$C_6$ haloalkylthio) carbonyl $C_1$–$C_6$ alkyl, ($C_3$–$C_6$ alkenylthio)carbonyl $C_1$–$C_6$ alkyl, ($C_3$–$C_6$ haloalkenylthio)carbonyl $C_1$–$C_6$ alkyl, ($C_3$–$C_6$ alkynylthio)carbonyl $C_1$–$C_6$ alkyl, ($C_3$–$C_6$ haloalkynylthio)carbonyl $C_1$–$C_6$ alkyl, ($C_3$–$C_8$ cycloalkylthio)carbonyl $C_1$–$C_6$ alkyl, ($C_3$–$C_8$ cyclohaloalkylthio)carbonyl $C_1$–$C_6$ alkyl, (($C_3$–$C_8$ cycloalkyl) $C_1$–$C_6$ alkylthio)carbonyl $C_1$–$C_6$ alkyl, di($C_1$–$C_6$ alkyl)C=NO carbonyl $C_1$–$C_6$ alkyl, (optionally substituted benzylthio)carbonyl $C_1$–$C_6$ alkyl, (optionally substituted phenylthio)carbonyl $C_1$–$C_6$ alkyl, hydroxy $C_2$–$C_6$ alkoxycarbonyl $C_1$–$C_6$ alkyl, ($C_1$–$C_6$ alkyl)carbonyloxy $C_2$–$C_6$ alkoxycarbonyl $C_1$–$C_6$ alkyl, ($C_1$–$C_6$ alkyl)carbonylamino $C_2$–$C_6$ alkoxycarbonyl $C_1$–$C_6$ alkyl, {($C_1$–$C_6$ alkoxy)carbonyl $C_1$–$C_6$ alkyl}oxycarbonyl $C_1$–$C_6$ alkyl, hydroxy $C_1$–$C_6$ alkyl, $C_1$–$C_6$ alkoxycarbonyl, $C_1$–$C_6$ haloalkoxycarbonyl, $C_3$–$C_8$ cycloalkoxycarbonyl, $C_3$–$C_6$ alkenyloxycarbonyl, benzyloxycarbonyl, $C_1$–$C_6$ alkylcarbonyl, optionally substituted benzyloxycarbonyl $C_1$–$C_6$ alkyl, optionally substituted phenoxycarbonyl $C_1$–$C_6$ alkyl, optionally substituted furyloxycarbonyl $C_1$–$C_6$ alkyl, optionally substituted furyl $C_1$–$C_6$ alkyloxycarbonyl $C_1$–$C_6$ alkyl, optionally substituted thienyloxycarbonyl $C_1$–$C_6$ alkyl, optionally substituted thienyl $C_1$–$C_6$ alkyloxycarbonyl $C_1$–$C_6$ alkyl, optionally substituted pyrrolyloxycarbonyl $C_1$–$C_6$ alkyl, optionally substituted pyrrolyl $C_1$–$C_6$ alkyloxycarbonyl $C_1$–$C_6$ alkyl, optionally substituted imidazoyloxycarbonyl $C_1$–$C_6$ alkyl, optionally substituted imidazoyl $C_1$–$C_6$ alkyloxycarbonyl $C_1$–$C_6$ alkyl, optionally substituted pyrazoyloxycarbonyl $C_1$–$C_6$ alkyl, optionally substituted pyrazoyl $C_1$–$C_6$ alkyloxycarbonyl $C_1$–$C_6$ alkyl, optionally substituted thiazoyloxycarbonyl $C_1$–$C_6$ alkyl, optionally substituted thiazoyl $C_1$–$C_6$ alkyloxycarbonyl $C_1$–$C_6$ alkyl, optionally substituted oxazoyloxycarbonyl $C_1$–$C_6$ alkyl, optionally substituted oxazoyl $C_1$–$C_6$ alkyloxycarbonyl $C_1$–$C_6$ alkyl, optionally substituted isothiazoyloxycarbonyl $C_1$–$C_6$ alkyl, optionally substituted isothiazoyl $C_1$–$C_6$ alkyloxycarbonyl $C_1$–$C_6$ alkyl, optionally substituted oxazoyloxycarbonyl $C_1$–$C_6$ alkyl, optionally substituted oxazoyl $C_1$–$C_6$ alkyloxycarbonyl $C_1$–$C_6$ alkyl, optionally substituted pyridyloxycarbonyl $C_1$–$C_6$ alkyl, optionally substituted pyridyl $C_1$–$C_6$ alkyloxycarbonyl $C_1$–$C_6$ alkyl, optionally substituted pyrazinyloxycarbonyl $C_1$–$C_6$ alkyl, optionally substituted pyrazinyl $C_1$–$C_6$ alkyloxycarbonyl $C_1$–$C_6$ alkyl, optionally substituted pyrimidinyloxycarbonyl $C_1$–$C_6$ alkyl, optionally substituted pyrimidinyl $C_1$–$C_6$ alkyloxycarbonyl $C_1$–$C_6$ alkyl, optionally substituted pyridazinyloxycarbonyl $C_1$–$C_6$ alkyl, optionally substituted pyridazinyl $C_1$–$C_6$ alkyloxycarbonyl $C_1$–$C_6$ alkyl, optionally substituted indolidinyloxycarbonyl $C_1$–$C_6$ alkyl, optionally substituted indolidinyl $C_1$–$C_6$ alkyloxycarbonyl $C_1$–$C_6$ alkyl, optionally substituted indolyloxycarbonyl $C_1$–$C_6$ alkyl, optionally substituted indolyl $C_1$–$C_6$ alkyloxycarbonyl $C_1$–$C_6$ alkyl, optionally substituted indazolyloxycarbonyl $C_1$–$C_6$ alkyl, optionally substituted indazolyl $C_1$–$C_6$ alkyloxycarbonyl $C_1$–$C_6$ alkyl, optionally substituted quinolyloxycarbonyl $C_1$–$C_6$ alkyl, optionally substituted quinolyl $C_1$–$C_6$ alkyloxycarbonyl $C_1$–$C_6$ alkyl, optionally substituted isoquinolyloxycarbonyl $C_1$–$C_6$ alkyl, optionally substituted isoquinolyl $C_1$–$C_6$ alkyloxycarbonyl $C_1$–$C_6$ alkyl, or a group of formula (3):

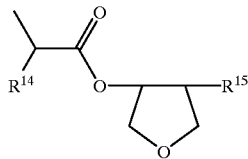

wherein $R^{14}$ is $C_1$–$C_5$ alkyl; $R^{15}$ is hydrogen, hydroxyl or a group of —O—$COR^{16}$; and $R^{16}$ is $C_1$–$C_6$ alkyl, $C_1$–$C_6$ haloalkyl, $C_3$–$C_6$ alkenyl, $C_3$–$C_8$ cycloalkyl, optionally substituted phenyl, optionally substituted benzyl or $C_1$–$C_6$ alkoxy, or a group of formula (4):

wherein $R^{17}$ is hydrogen, halogen or $C_1$–$C_6$ alkyl; $R^{18}$ is $C_3$–$C_8$ cycloalkyl, benzyl, $C_2$–$C_{10}$ alkyl with an epoxide group, $C_3$–$C_8$ cycloalkyl $C_1$–$C_6$ alkyl, $C_3$–$C_8$ cycloalkyl $C_2$–$C_6$ alkenyl, $C_1$–$C_6$ alkyl substituted with $OR^{19}$ and $OR^{20}$ on the same carbon atom, $C_2$–$C_6$ alkenyl substituted with $OR^{19}$ and $OR^{20}$ on the same carbon atom, $C_1$–$C_6$ alkyl substituted with $SR^{19}$ and $SR^{20}$ on the same carbon atom, $C_2$–$C_6$ alkenyl substituted with $SR^{19}$ and $SR^{20}$ on the same carbon atom, carboxy $C_2$–$C_6$ alkenyl, ($C_1$–$C_8$ alkoxy)carbonyl $C_2$–$C_6$ alkenyl, ($C_1$–$C_8$ haloalkoxy)carbonyl $C_2$–$C_6$ alkenyl, {($C_1$–$C_4$ alkoxy) $C_1$–$C_4$ alkoxy}carbonyl $C_2$–$C_6$ alkenyl or ($C_3$–$C_8$ cycloalkoxy)carbonyl $C_2$–$C_6$ alkenyl; $R^{19}$ and $R^{20}$ are independently $C_1$–$C_6$ alkyl or $C_1$–$C_6$ haloalkyl, or $R^{19}$ and $R^{20}$ are taken together with to form ethylene optionally substituted with halogen, trimethylene optionally substituted with halogen, tetramethylene optionally substituted with halogen, pentamethylene optionally substituted with halogen, or ethyleneoxyethylene optionally substituted with halogen;

$R^{21}$ is $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl or benzyl;

$R^{22}$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_1$–$C_6$ alkyl)carbonyl $C_1$–$C_6$ alkyl, ($C_1$–$C_6$ haloalkyl)carbonyl $C_1$–$C_6$ alkyl, {($C_1$–$C_4$ alkoxy) $C_1$–$C_4$ alkyl}carbonyl $C_1$–$C_6$ alkyl, ($C_3$–$C_8$ cycloalkyl)carbonyl $C_1$–$C_6$ alkyl, —$CH_2COON(R^{26})R^{27}$, —$CH(C_1$–$C_4$ alkyl)$COON(R^{26})R^{27}$, —$CH_2CON(R^{26})R^{27}$, —$CH(C_1$–$C_4$ alkyl)$CON(R^{26})R^{27}$, {($C_1$–$C_6$ alkoxy)carbonyl $C_1$–$C_6$ alkyl}oxycarbonyl $C_1$–$C_6$ alkyl or hydroxy $C_1$–$C_6$ alkyl;

$R^{26}$ and $R^{27}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl or {($C_1$–$C_4$ alkoxy) $C_1$–$C_4$ alkyl}carbonyl $C_1$–$C_6$ alkyl, or $R^{26}$ and $R^{27}$ are taken together to form tetramethylene, pentamethylene or ethyleneoxyethylene;

$R^{23}$ and $R^{24}$ are independently hydrogen, halogen or $C_1$–$C_6$ alkyl; and $R^{25}$ is hydrogen, $C_1$–$C_6$ alkyl, $C_1$–$C_6$ haloalkyl, $C_3$–$C_8$ cycloalkyl or $C_3$–$C_6$ alkenyl.

In the above definition of the present compounds, the respective substituents are exemplified as follows:

Examples of the halogen represented by X and Y may include fluorine, chlorine, bromine and iodine.

Examples of the $C_1$–$C_6$ alkyl represented by R may include methyl, ethyl, propyl, isopropyl and butyl.

Examples of the $C_1$–$C_3$ alkyl represented by $R^2$ and $R^3$ may include methyl and ethyl.

Examples of the $C_1$–$C_6$ alkyl represented by $R^1$ may include methyl, ethyl, propyl, isopropyl, butyl, isobutyl, t-butyl, amyl, isoamyl and t-amyl, wherein "t-" means "tertiary-" and is hereinafter used in the same meaning.

Examples of the $C_1$–$C_6$ haloalkyl represented by $R^1$ may include 2-chloroethyl, 2-bromoethyl and 2,2,2-trifluoroethyl.

Examples of the $C_3$–$C_8$ cycloalkyl represented by $R^1$ may include cyclopropyl, cyclobutyl, cyclopentyl and cyclohexyl.

Examples of the $C_3$–$C_6$ alkenyl represented by R 1 may include allyl, 1-methyl-2-propenyl, 3-butenyl, 2-butenyl, 3-methyl-2-butenyl and 2-methyl-3-butenyl.

Examples of the $C_3$–$C_6$ haloalkenyl represented by $R^1$ may include 2-chloro-2-propenyl and 3,3-dichloro-2-propenyl.

Examples of the $C_3$–$C_6$ alkynyl represented by $R^1$ may include propargyl, 1-methyl-2-propynyl, 2-butynyl and 1,1-dimethyl-2-propynyl.

Examples of the $C_3$–$C_6$ haloalkynyl represented by $R^1$ may include 3-bromopropargyl.

Examples of the cyano $C_1$–$C_6$ alkyl represented by $R^1$ may include cyanomethyl.

Examples of the $C_1$–$C_4$ alkoxy $C_1$–$C_4$ alkyl represented by $R^1$ may include methoxymethyl, methoxyethyl, ethoxymethyl and ethoxyethyl.

Examples of the $C_1$–$C_4$ alkylthio $C_1$–$C_4$ alkyl represented by $R^1$ may include methylthiomethyl and methylthioethyl.

Examples of the carboxy $C_1$–$C_6$ alkyl represented by $R^1$ may include carboxymethyl, 1-carboxyethyl and 2-carboxyethyl.

Examples of the ($C_1$–$C_8$ alkoxy)carbonyl $C_1$–$C_6$ alkyl represented by $R^1$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl and 1-t-amyloxycarbonylethyl.

Examples of the {($C_1$–$C_4$ alkoxy) $C_1$–$C_4$ alkoxy}carbonyl $C_1$–$C_6$ alkyl represented by $R^1$ may include methoxymethoxycarbonylmethyl, methoxyethoxycarbonylmethyl and 1-methoxyethoxycarbonylethyl.

Examples of the ($C_3$–$C_8$ cycloalkoxy)carbonyl $C_1$–$C_6$ alkyl represented by $R^1$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl and 1-cyclohexyloxycarbonylethyl.

Examples of the $C_1$–$C_6$ alkoxycarbonyl represented by $R^1$ may include methoxycarbonyl, ethoxycarbonyl, propoxycarbonyl, butoxycarbonyl, isopropoxycarbonyl, isobutoxycarbonyl and t-butoxycarbonyl.

Examples of the $C_1$–$C_6$ haloalkoxycarbonyl represented by $R^1$ may include 2,2,2-trichloroethylcarbonyl.

Examples of the $C_3$–$C_8$ cycloalkoxycarbonyl represented by $R^1$ may include cyclopropyloxycarbonyl and cyclobutyloxycarbonyl.

Examples of the $C_3$–$C_6$ alkenyloxycarbonyl represented by $R^1$ may include allyloxycarbonyl.

Examples of the {($C_1$–$C_6$ alkoxy)carbonyl $C_1$–$C_6$ alkyl}oxycarbonyl $C_1$–$C_6$ alkyl represented by $R^1$ may include (methoxycarbonyl)methoxycarbonylmethyl and (ethoxycarbonyl)methoxycarbonylmethyl.

Examples of the $C_1$–$C_6$ alkyl represented by $R^{12}$ and $R^{13}$ may include methyl, ethyl, propyl and isopropyl.

Examples of the $C_1$–$C_3$ alkyl represented by $R^4$ may include methyl.

Examples of the $C_1$–$C_6$ alkyl represented by $R^5$ may include methyl, ethyl, propyl, isopropyl, isobutyl, butyl and isoamyl.

Examples of the $C_1$–$C_6$ haloalkyl represented by $R^5$ may include 2-chloroethyl, 2-bromoethyl, 3-chlorobutyl, 3-bromobutyl and difluoromethyl.

Examples of the ($C_3$–$C_8$ cycloalkyl) $C_1$–$C_6$ alkyl represented by $R^5$ may include cyclopentylmethyl.

Examples of the $C_3$–$C_6$ alkenyl represented by $R^5$ may include allyl, 1-methyl-2-propenyl, 3-butenyl, 2-butenyl, 3-methyl-2-butenyl and 2-methyl-3-butenyl.

Examples of the $C_3$–$C_6$ haloalkenyl represented by $R^5$ may include 2-chloro-2-propenyl and 3,3-dichloro-2-propenyl.

Examples of the $C_3$–$C_6$ alkynyl represented by $R^5$ may include propargyl, 1-methyl-2-propynyl, 2-butynyl, 3-butynyl and 1,1-dimethyl-2-propynyl.

Examples of the $C_3$–$C_6$ haloalkynyl represented by $R^5$ may include 3-iodo-2-propynyl and 3-bromo-2-propynyl.

Examples of the cyano $C_1$–$C_6$ alkyl represented by $R^5$ may include cyanomethyl.

Examples of the $C_1$–$C_4$ alkoxy $C_1$–$C_4$ alkyl represented by $R^5$ may include methoxymethyl, 1-methoxyethyl and ethoxymethyl.

Examples of the carboxy $C_1$–$C_6$ alkyl represented by $R^5$ may include carboxymethyl, 1-carboxyethyl and 2-carboxyethyl.

Examples of the ($C_1$–$C_6$ alkoxy)carbonyl $C_1$–$C_6$ alkyl represented by $R^5$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl and 1-t-butoxycarbonylethyl.

Examples of the {($C_1$–$C_4$ alkoxy) $C_1$–$C_4$ alkoxy} carbonyl $C_1$–$C_6$ alkyl represented by $R^5$ may include methoxyethoxycarbonylmethyl and 1-methoxymethoxycarbonylethyl.

Examples of the ($C_3$–$C_8$ cycloalkoxy)carbonyl $C_1$–$C_6$ alkyl represented by $R^5$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl and 1-cyclohexyloxycarbonylethyl.

Examples of the hydroxy $C_1$–$C_6$ alkyl represented by $R^5$ may include hydroxymethyl, hydroxyethyl and hydroxypropyl.

Examples of the $C_1$–$C_6$ alkyl represented by $R^6$ may include methyl and ethyl.

Examples of the $C_1$–$C_6$ haloalkyl represented by $R^6$ may include bromomethyl, dibromomethyl, tribromomethyl, 1-bromoethyl, chloromethyl, dichloromethyl and trichloromethyl.

Examples of the hydroxy $C_1$–$C_6$ alkyl represented by $R^6$ may include hydroxymethyl.

Examples of the ($C_1$–$C_6$ alkoxy) $C_1$–$C_6$ alkyl represented by $R^6$ may include methoxymethyl, ethoxymethyl, propoxymethyl and isopropoxymethyl.

Examples of the {($C_1$–$C_6$ alkoxy) $C_1$–$C_6$ alkoxy} $C_1$–$C_6$ alkyl represented by $R^6$ may include methoxymethoxymethyl, methoxyethoxymethyl and ethoxymethoxymethyl.

Examples of the ($C_1$–$C_6$ alkyl)carbonyloxy $C_1$–$C_6$ alkyl) represented by $R^6$ may include acetyloxymethyl, ethylcarbonyloxymethyl and isopropylcarbonyloxymethyl.

Examples of the ($C_1$–$C_6$ haloalkyl)carbonyloxy $C_1$–$C_6$ alkyl represented by $R^6$ may include trifluoroacetyloxymethyl, chloroacetyloxymethyl and trichloroacetyloxymethyl.

Examples of the ($C_1$–$C_6$ alkoxy)carbonyl represented by $R^6$ may include methoxycarbonyl, ethoxycarbonyl, propoxycarbonyl, butoxycarbonyl, amyloxycarbonyl, isopropoxycarbonyl, isobutoxycarbonyl and isoamyloxycarbonyl.

Examples of the $C_1$–$C_6$ alkyl represented by $R^7$ may include methyl.

Examples of the $C_1$–$C_6$ alkyl represented by $R^8$ may include methyl and ethyl.

Examples of the $C_1$–$C_6$ haloalkyl represented by $R^8$ may include chloromethyl and bromomethyl.

Examples of the $C_1$–$C_6$ hydroxyalkyl represented by $R^8$ may include hydroxymethyl.

Examples of the $C_1$–$C_4$ alkoxy $C_1$–$C_4$ alkyl represented by $R^8$ may include methoxymethyl, ethoxymethyl, isopropoxymethyl, butoxymethyl and isobutoxymethyl.

Examples of the $C_1$–$C_3$ alkoxy $C_1$–$C_3$ alkoxy $C_1$–$C_3$ alkyl represented by $R^8$ may include methoxymethoxymethyl, methoxyethoxymethyl and ethoxymethoxymethyl.

Examples of the ($C_1$–$C_6$ alkyl)carbonyloxy $C_1$–$C_6$ alkyl represented by $R^8$ may include acetyloxymethyl, ethylcarbonyloxymethyl and isopropylcarbonyloxymethyl.

Examples of the ($C_1$–$C_6$ haloalkyl)carbonyl $C_1$–$C_6$ alkyl represented by $R^8$ may include 2-chloroethylcarbonyloxymethyl.

Examples of the carboxy $C_1$–$C_6$ alkyl represented by $R^8$ may include carboxymethyl.

Examples of the ($C_1$–$C_8$ alkoxy)carbonyl represented by $R^8$ may include methoxycarbonyl, ethoxycarbonyl, propoxycarbonyl, butoxycarbonyl, amyloxycarbonyl, isopropoxycarbonyl, isobutoxycarbonyl and isoamyloxycarbonyl.

Examples of the ($C_1$–$C_6$ haloalkoxy)carbonyl represented by $R^8$ may include 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dicholoroethoxycarbonyl, 2,2,2-trifluoroethoxycarbonyl, 2,2,2-trichloroethoxycarbonyl and 2,2,2-tribromoethoxycarbonyl.

Examples of the ($C_3$–$C_{10}$ cycloalkoxy)carbonyl represented by $R^8$ may include cyclobutyloxycarbonyl, cyclopentyloxycarbonyl and cyclohexyloxycarbonyl.

Examples of the ($C_3$–$C_8$ alkenyloxy)carbonyl represented by $R^8$ may include allyloxycarbonyl, 3-butenyloxycarbonyl and 1-methyl-2-propenyloxycarbonyl.

Examples of the ($C_3$–$C_8$ alkynyloxy)carbonyl represented by $R^8$ may include propargyloxycarbonyl, 3-butynyloxycarbonyl and 1-methyl-2-propynyloxycarbonyl.

Examples of the ($C_1$–$C_6$ alkyl)aminocarbonyl represented by $R^8$ may include methylaminocarbonyl, ethylaminocarbonyl and propylaminocarbonyl.

Examples of the di($C_1$–$C_6$ alkyl)aminocarbonyl represented by $R^8$ may include dimethylaminocarbonyl, diethylaminocarbonyl and diisopropylaminocarbonyl.

Examples of the ($C_1$–$C_6$ alkyl)aminocarbonyloxy $C_1$–$C_6$ alkyl represented by $R^8$ may include methylaminocarbonyloxymethyl, ethylaminocarbonyloxymethyl and propylaminocarbonyloxymethyl.

Examples of the di($C_1$–$C_6$ alkyl)aminocarbonyloxy $C_1$–$C_6$ alkyl represented by $R^8$ may include dimethylaminocarbonyloxymethyl and diethylaminocarbonyloxymethyl.

Examples of the $C_1$–$C_6$ alkyl represented by $R^{22}$ may include methyl, ethyl, propyl, isopropyl, isobutyl, butyl, t-butyl, amyl, isoamyl and t-amyl.

Examples of the $C_1$–$C_6$ haloalkyl represented by $R^{22}$ may include 2-chloroethyl, 2-bromoethyl and 2,2,2-trifluoroethyl.

Examples of the $C_3$–$C_8$ cycloalkyl represented by $R^{22}$ may include cyclopropyl, cyclobutyl, cyclopentyl and cyclohexyl.

Examples of the $C_3$–$C_6$ alkenyl represented by $R^{22}$ may include allyl, 1-methyl-2-propenyl, 3-butenyl, 2-butenyl, 3-methyl-2-butenyl and 2-methyl-3-butenyl.

Examples of the $C_3$–$C_6$ haloalkenyl represented by $R^{22}$ may include 2-chloro-2-propenyl and 3,3-dichloro-2-propenyl.

Examples of the $C_3$–$C_6$ alkynyl represented by $R^{22}$ may include propargyl, 1-methyl-2-propynyl and 2-butynyl.

Examples of the $C_3$–$C_6$ haloalkynyl represented by $R^{22}$ may include 3-bromopropargyl.

Examples of the cyano $C_1$–$C_6$ alkyl represented by $R^{22}$ may include cyanoethyl.

Examples of the $C_1$–$C_4$ alkoxy $C_1$–$C_4$ alkyl represented by $R^{22}$ may include methoxymethyl, methoxyethyl, ethoxymethyl and ethoxyethyl.

Examples of the $C_1$–$C_4$ alkylthio $C_1$–$C_4$ alkyl represented by $R^{22}$ may include methylthioethyl.

Examples of the carboxy $C_1$–$C_6$ alkyl represented by $R^{22}$ may include carboxymethyl, 1-carboxyethyl and 2-carboxyethyl.

Examples of the ($C_1$–$C_8$ alkoxy)carbonyl $C_1$–$C_6$ alkyl represented by $R^{22}$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl and 1-t-amyloxycarbonylethyl.

Examples of the {($C_1$–$C_4$ alkoxy) $C_1$–$C_4$ alkoxy}carbonyl $C_1$–$C_6$ alkyl represented by $R^{22}$ may include methoxymethoxycarbonylmethyl, methoxyethoxycarbonylmethyl and 1-methoxyethoxycarbonylethyl.

Examples of the ($C_3$–$C_8$ cycloalkoxy)carbonyl $C_1$–$C_6$ alkyl represented by $R^{22}$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl and 1-cyclohexyloxycarbonylethyl.

Examples of the $C_1$–$C_6$ alkyl represented by $R^{23}$ and $R^{24}$ may include methyl.

Examples of the halogen represented by $R^{23}$ and $R^{24}$ may include chlorine and bromine.

Examples of the $C_1$–$C_6$ alkyl represented by $R^{25}$ may include methyl, ethyl, propyl, isopropyl, isobutyl, butyl, t-butyl, amyl, isoamyl and t-amyl.

Examples of the $C_1$–$C_6$ haloalkyl represented by $R^{25}$ may include 2-chloroethyl, 2-bromoethyl and 2,2,2-trifluoroethyl.

Examples of the $C_3$–$C_8$ cycloalkyl represented by $R^{25}$ may include cyclopropyl, cyclobutyl, cyclopentyl and cyclohexyl.

Examples of the $C_3$–$C_6$ alkenyl represented by $R^{25}$ may include allyl, 1-methyl-2-propenyl, 3-butenyl, 2-butenyl, 3-methyl-2-butenyl and 2-methyl-3-butenyl.

Examples of the $C_1$–$C_6$ alkyl represented by $R^{26}$ and $R^{27}$ may include methyl, ethyl, propyl and isopropyl.

The present compounds have geometrical isomers based on the double bond, optical isomers and diastereomers based on the presence of at least one asymmetric carbon atom, and these isomers and mixtures thereof are, of course, included within the scope of the present invention.

The following illustrates the process for producing the present compounds.

The present compounds can be produced by reacting hydrazone compounds of formula (5):

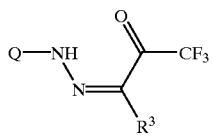

wherein $R^3$ and Q are as defined above, with malonic acid monoester derivatives of formula (6):

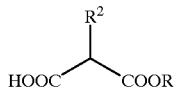

wherein R and $R^2$ are as defined above, in the presence of a base, which process is hereinafter referred to as process 1.

Process 1 can be carried out under the reaction conditions described in the following process 1-1 or 1-2.

I) Process 1-1 in which the hydrazone compounds of formula (5) are reacted with the malonic acid monoester derivatives of formula (6) in the presence of a secondary amine combined with pyridine and/or quinoline.

The reaction is usually effected in pyridine and/or quinoline. The reaction temperature is usually in the range of 40° to 140° C., preferably 60° to 100° C. The reaction time is usually in the range of a moment to 24 hours, preferably 1 to 5 hours.

The amounts of reagents to be used in the reaction are usually 1 to 10 moles of the malonic acid monoester derivative of formula (6) and usually 0.1 to 5 moles, preferably 0.8 to 2 moles, and more preferably 1 to 2 moles of the secondary amine, for each one mole of the hydrazone compound of formula (5).

Examples of the secondary amine used in the reaction may include cyclic anines such as piperidine, morpholine and pyrrolidine; and dialkylamines such as diethylamine and diisopropylamine.

Furthermore, co-solvents can also be used in the reaction, examples of which may include aliphatic hydrocarbons such as hexane, heptane, ligroin and petroleum ether; aromatic hydrocarbons such as benzene, toluene and xylene; halogenated hydrocarbons such as dichloromethane, chloroform, carbon tetrachloride, 1,2-dichloroethane, 1,1,1-trichloroethane, chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; nitrites such as acetonitrile and isobutyronitrile; esters such as ethyl acetate and butyl acetate; alcohols such as methanol, ethanol, propanol, butanol and isopropanol; acid amides such as N,N-dimethylformamide; sulfur compounds such as dimethylsulfoxide and sulforane; and mixtures thereof.

II) Process 1-2 in which the hydrazone compounds of formula (5) are reacted with the malonic acid monoester derivatives of formula (6) in the presence of a base.

The reaction is usually effected without solvent or in a solvent. The reaction temperature is usually in the range of 20° to 200° C., preferably 40° to 150° C. The reaction time is usually in the range of a moment to 72 hours.

The amounts of reagents to be used in the reaction are usually 1 to 10 moles, preferably 1 to 2 moles, of the malonic acid monoester derivative of formula (6) for each one mole of the hydrazone compound of formula (5), and usually 1 mole to a larger excess, preferably 1 to 10 moles, of the base for each one mole of the malonic acid monoester derivative of formula (6).

Examples of the base used in the reaction may include organic bases, preferably tertiary amines such as dialkylaniline derivatives, e.g., N,N-dimethylaniline and N,N-diethylaniline; triethylamine, diisopropylethylamine, tri-n-propylamine, tri-n-butylamine, benzyldimethylamine, phenethyldimethylamine, N-methylmorpholine, 1,8-diazabicyclo[5.4.0]undec-7-ene, 1,5-diazabicyclo[4.3.0]non-5-ene and 1,4-diazabicyclo[2.2.2]octane. Preferred are trialkylamines such as triethylamine, diisopropylethylamine, tri-n-propylamine and tri-n-butylamine.

Examples of the solvent used in the reaction may include aliphatic hydrocarbons such as hexane, heptane, ligroin and petroleum ether; aromatic hydrocarbons such as benzene, toluene and xylene; halogenated hydrocarbons such as dichloromethane, chloroform, carbon tetrachloride, 1,2-dichloroethane, 1,1,1-trichloroethane, chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; nitrogen-containing aromatic compounds such as pyridine and quinoline; acid amides such as N,N-dimethylformamide; esters such as ethyl acetate and butyl acetate; ketones such as acetone, methyl ethyl ketone, methyl isobutyl ketone and cyclohexanone; nitriles such as acetonitrile and isobutyronitrile; alcohols such as methanol, ethanol, propanol, butanol and isopropanol; water; and mixtures thereof.

After completion of the reaction, the reaction mixture is directly concentrated or subjected to post-treatments that the reaction mixture is poured into an aqueous solution of a mineral acid such as hydrochloric acid or diluted sulfuric acid, which is then extracted with an organic solvent, and the organic layer is dried and concentrated. If necessary, purification is subsequently carried out by a technique such as recrystallization or column chromatography. Thus, the present compounds can be obtained.

The present compounds are usually obtained as a mixture of diastereomers. These diastereomers can be used as the starting material in the subsequent reaction without particular separation or after fine separation by chromatography.

The malonic acid monoester derivatives of formula (6) used in the above production process can be produced by hydrolyzing the corresponding malonic acid diesters in the presence of a base.

The reaction is usually effected in a solvent. The reaction temperature is usually in the range of 0° to 110° C. The reaction time is usually in the range of a moment to 72 hours.

The amount of base to be used in the reaction is usually 1 mole for each one mole of the malonic acid diester as the starting material, which is the stoichiometric ratio, and it is preferred to use 1 mole of the base.

Examples of the base used in the reaction may include inorganic bases such as sodium hydroxide and potassium hydroxide.

Examples of the solvent used in the reaction may include aliphatic hydrocarbons such as hexane, heptane, ligroin and petroleum ether; aromatic hydrocarbons such as benzene, toluene and xylene; ethers such as diethyl ether, diisopropyl ether, 1,4-dioxane, tetrahydrofuran, ethylene glycol dimethyl ether and methyl t-butyl ether; alcohols such as methanol, ethanol, ethylene glycol and isopropanol; water; and mixtures thereof After completion of the reaction, the reaction mixture is subjected to post-treatments that the reaction mixture is poured into an aqueous solution of a mineral acid such as hydrochloric acid or diluted sulfuric acid, which is then extracted with an organic solvent, and the organic layer is dried and concentrated. If necessary, purification is subsequently carried out by a technique such as recrystallization or column chromatography. Thus, the malonic acid monoester derivatives of formula (6) can be obtained.

The hydrazone compounds of formula (5) can be produced by reacting compounds of formula (8):

$$CF_3C(=O)CV_2R^3$$

wherein $R^3$ is as defined above and V is iodine, bromine or chlorine, with water in the presence of a base to give carbonyl compounds of formula (9):

$$CF_3C(=O)C(=O)R^3$$

wherein $R^3$ is as defined above, or hydrates or acetal derivatives thereof, which reaction is hereinafter referred to as reaction 1; and then reacting the carbonyl compounds of formula (9), or hydrates or acetal derivatives thereof, with hydrazine derivatives of formula (10):

$$Q-NHNH_2$$

wherein Q is as defined above, which reaction is hereinafter referred to as reaction 2.

Reaction 1 is usually effected in a solvent. The reaction temperature is usually in the range of 0° to 100° C. The reaction time is usually in the range of a moment to 72 hours.

The amounts of reagents to be used in the reaction are usually 2 moles of water and usually 2 moles of the base for each one mole of the compound of formula (8), which is the stoichiometric ratio. If necessary, these reagents can be used in excess.

As the base, either organic bases or inorganic bases can be used, examples of which may include sodium acetate and potassium acetate.

The carbonyl compounds of formula (9) can also be reacted in the form of hydrates or acetal derivatives in the presence of water or an alcohol.

Reaction 2 is usually effected in a solvent. The reaction temperature is usually in the range of 0° to 100° C. The reaction time is usually in the range of a moment to 72 hours.

The amount of reagent to be used in the reaction is usually 1 mole of the hydrazine derivative of formula (10) for each one mole of the compound of formula (8) used in process 1, which is the stoichiometric ratio. If necessary, the compound of formula (8) can be used in excess. The hydrazine derivative of formula (10) can also be used in the form of salts such as hydrochloride or sulfate salts.

Examples of the solvent used in reactions 1 and 2 may include aliphatic hydrocarbons such as hexane, heptane, ligroin and petroleum ether; aromatic hydrocarbons such as benzene, toluene and xylene; halogenated hydrocarbons such as chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; esters such as ethyl acetate and butyl acetate; nitriles such as acetonitrile and isobutyronitrile; alcohols such as methanol, ethanol, ethylene glycol and isopropanol; water; and mixtures thereof.

After completion of the reaction, water is added, if necessary, to the reaction mixture and the resulting crystals are collected by filtration, or the reaction mixture is subjected to ordinary post-treatments such as extraction with an organic solvent and concentration. If necessary, purification is subsequently carried out by a technique such as chromatography or recrystallization. Thus, the desired products can be isolated.

The hydrazine derivatives of formula (10) can be produced by diazotizing aniline derivatives of formula (11):

$$Q-NH_2$$

wherein Q is as defined above, with nitrous acid, sodium nitrite or other agents under acidic conditions, and then reducing the diazonium salts with stannous chloride or other agents (see, e.g., Organic Synthesis Collective Volume 1, p. 442).

The aniline derivatives of formula (11) are known in, for example, European Patent Publication No. 61741-A, U.S. Pat. Nos. 4,670,046, 4,770,695, 4,709,049, 4,640,707, 4,720,297 and 5,169,431, and Japanese Patent Laid-open Publication No. 63-156787, or can be produced according to the methods as described therein.

The hydrazone compounds of formula (5) can also be produced from the aniline derivatives of formula (11) according to the following scheme:

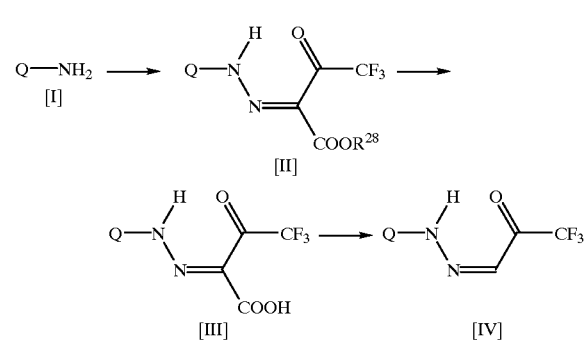

wherein Q is as defined above and $R^{28}$ is $C_1$–$C_6$ alkyl.

The reactions in the respective steps are effected, for example, as follows:

(1) Step of Producing Compound [II] from Compound [I]

Compound [II] can be produced by reacting compound [I] with a nitrite salt such as sodium nitrite or potassium nitrite in water under acidic conditions to give the corresponding diazonium salt, and then reacting the diazonium salt with a compound of formula (12):

$$CF_3C(=O)CH_2C(=O)OR^{28}$$

wherein Q and $R^{28}$ are as defined above, in the presence of a base such as sodium acetate or pyridine (see Tetrahedron, vol. 35, p. 2013 (1979)).

(2) Step of Producing Compound [III] from Compound [II]

Compound [III] can be usually produced by hydrolyzing compound [II] in the presence of a base in a solvent.

The reaction temperature is usually in the range of 0° to 100° C. The reaction time is usually in the range of a moment to 24 hours.

The amount of reagent to be used in the reaction is usually 1 mole of the base for each one mole of compound [II], which is the stoichiometric ratio; however, it can be changed, if necessary.

Examples of the base used in the reaction may include inorganic bases such as sodium hydroxide, lithium hydroxide, lithium hydroxide monohydrate, barium hydroxide and potassium hydroxide.

Examples of the solvent used in the reaction may include aliphatic hydrocarbons such as hexane, heptane, ligroin and petroleum ether; aromatic hydrocarbons such as benzene, toluene and xylene; halogenated hydrocarbons such as chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; alcohols such as methanol, ethanol, ethylene glycol and isopropanol; water; and mixtures thereof.

(3) Step of Producing Compound [IV] from Compound [III]

Compound [IV] can be produced by heating compound [III] in a solvent to cause decarbonization.

The reaction temperature is usually in the range of 50° to 200° C. The reaction time is usually in the range of a moment to 72 hours.

Examples of the solvent used in the reaction may include aliphatic hydrocarbons such as hexane, heptane, ligroin and petroleum ether; aromatic hydrocarbons such as benzene, toluene and xylene; halogenated hydrocarbons such as chloroform, carbon tetrachloride, 1,2-dichloroethane, chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; ketones such as acetone, methyl ethyl ketone, methyl isobutyl ketone and cyclohexanone; acid amides such as N,N-dimethylformamide; tertiary amines such as triethylamine, diisopropylethylamine, N,N-dimethylaniline, N,N-diethylaniline and N-methylmorpholine; nitrogen-containing aromatic compounds such as pyridine and picoline; sulfur-containing compounds such as dimethylsulfoxide and sulforane; fatty acids such as formic acid, acetic acid and propionic acid; alcohols such as methanol, ethanol, ethylene glycol and isopropanol; water; and mixtures thereof.

The reaction can also be effected, if necessary, with a metal catalyst such as copper.

After completion of the reaction, the reaction mixture is filtered for collection of the resulting crystals or subjected to ordinary post-treatments such as extraction with an organic solvent and concentration. If necessary, purification is subsequently carried out by a technique such as chromatography or recrystallization. Thus, the desired products can be isolated.

The hydrazone compound [IV] wherein Q is Q-1, B is $OR^1$ or $SR^1$, and $R^1$ is carboxy $C_1$–$C_6$ alkyl can also be produced by the hydrolysis and decarbonization of compound [II] wherein Q is Q-1, B is $OR^1$ or $SR^1$, and $R^1$ is ($C_1$–$C_8$ alkoxy)carbonyl $C_1$–$C_6$ alkyl.

Tables 1 to 21 show the present compounds obtained by the above production process, and Tables 22 and 23 show the hydrazone compounds of formula (5) and the malonic acid monoester derivatives of formula (6), respectively, which are used in process 1. These compounds are to be construed as merely illustrative and not limitations of the present invention. In these tables, "c-" means cyclo-; "i-" iso-; "Et" ethyl; and "Bu" butyl.

Compounds of formula (13):

TABLE 1

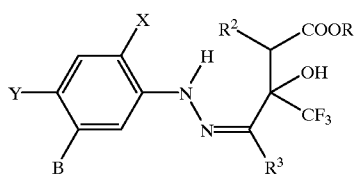

| Compound | X | Y | R | $R^2$ | $R^3$ | B |
|---|---|---|---|---|---|---|
| 1-1 | F | Cl | $CH_3$ | $CH_3$ | H | H |

TABLE 1-continued

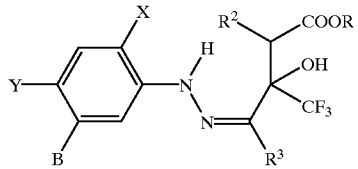

| Compound | X | Y | R | $R^2$ | $R^3$ | B |
|---|---|---|---|---|---|---|
| 1-2 | F | Cl | $CH_3$ | $CH_3$ | H | OH |
| 1-3 | F | Cl | $CH_3$ | $CH_3$ | H | $OCH_3$ |
| 1-4 | F | Cl | $CH_3$ | $CH_3$ | H | $OC_2H_5$ |
| 1-5 | F | Cl | $CH_3$ | $CH_3$ | H | $OCH(CH_3)_2$ |
| 1-6 | F | Cl | $CH_3$ | $CH_3$ | H | $OCH_2CH=CH_2$ |
| 1-7 | F | Cl | $CH_3$ | $CH_3$ | H | $OCH_2C\equiv CH$ |
| 1-8 | F | Cl | $CH_3$ | $CH_3$ | H | $OCH(CH_3)C\equiv CH$ |
| 1-9 | F | Cl | $CH_3$ | $CH_3$ | H | $OCH_2COOH$ |
| 1-10 | F | Cl | $CH_3$ | $CH_3$ | H | $OCH_2COOCH_3$ |
| 1-11 | F | Cl | $CH_3$ | $CH_3$ | H | $OCH_2COOC_2H_5$ |
| 1-12 | F | Cl | $CH_3$ | $CH_3$ | H | $OCH_2COOC_3H_7$ |
| 1-13 | F | Cl | $CH_3$ | $CH_3$ | H | $OCH_2COOC_4H_9$ |
| 1-14 | F | Cl | $CH_3$ | $CH_3$ | H | $OCH_2COOC_5H_{11}$ |
| 1-15 | F | Cl | $CH_3$ | $CH_3$ | H | $OCH_2COO$-i-$C_3H_7$ |
| 1-16 | F | Cl | $CH_3$ | $CH_3$ | H | $OCH_2COO$-i-$C_4H_9$ |
| 1-17 | F | Cl | $CH_3$ | $CH_3$ | H | $OCH_2COO$-c-$C_5H_9$ |
| 1-18 | F | Cl | $CH_3$ | $CH_3$ | H | $OCH_2COO$-c-$C_6H_{11}$ |
| 1-19 | F | Cl | $CH_3$ | $CH_3$ | H | $OCH(CH_3)COOH$ |
| 1-20 | F | Cl | $CH_3$ | $CH_3$ | H | $OCH(CH_3)COOCH_3$ |
| 1-21 | F | Cl | $CH_3$ | $CH_3$ | H | $OCH(CH_3)COOC_2H_5$ |
| 1-22 | F | Cl | $CH_3$ | $CH_3$ | H | $OCH(CH_3)COOC_3H_7$ |
| 1-23 | F | Cl | $CH_3$ | $CH_3$ | H | $OCH(CH_3)COOC_4H_9$ |
| 1-24 | F | Cl | $CH_3$ | $CH_3$ | H | $OCH(CH_3)COOC_5H_{11}$ |
| 1-25 | F | Cl | $CH_3$ | $CH_3$ | H | $OCH(CH_3)COO$-i-$C_3H_7$ |
| 1-26 | F | Cl | $CH_3$ | $CH_3$ | H | $OCH(CH_3)COO$-i-$C_4H_9$ |

TABLE 2

| Compound | X | Y | R | $R^2$ | $R^3$ | B |
|---|---|---|---|---|---|---|
| 1-27 | F | Cl | $CH_3$ | $CH_3$ | H | $OCH(CH_3)COO$-c-$C_5H_9$ |
| 1-28 | F | Cl | $CH_3$ | $CH_3$ | H | $OCH(CH_3)COO$-c-$C_6H_{11}$ |
| 1-29 | F | Cl | $CH_3$ | $CH_3$ | H | O-c-$C_5H_9$ |
| 1-30 | F | Cl | $CH_3$ | $CH_3$ | H | O-c-$C_6H_{11}$ |
| 1-31 | F | Cl | $CH_3$ | $CH_3$ | H | $SCH_2C\equiv CH$ |
| 1-32 | F | Cl | $CH_3$ | $CH_3$ | H | $SCH(CH_3)C\equiv CH$ |
| 1-33 | F | Cl | $CH_3$ | $CH_3$ | H | $SCH_2COOH$ |
| 1-34 | F | Cl | $CH_3$ | $CH_3$ | H | $SCH_2COOCH_3$ |
| 1-35 | F | Cl | $CH_3$ | $CH_3$ | H | $SCH_2COOC_2H_5$ |
| 1-36 | F | Cl | $CH_3$ | $CH_3$ | H | $SCH_2COOC_3H_7$ |
| 1-37 | F | Cl | $CH_3$ | $CH_3$ | H | $SCH_2COOC_4H_9$ |
| 1-38 | F | Cl | $CH_3$ | $CH_3$ | H | $SCH_2COOC_5H_{11}$ |
| 1-39 | F | Cl | $CH_3$ | $CH_3$ | H | $SCH_2COO$-i-$C_3H_7$ |
| 1-40 | F | Cl | $CH_3$ | $CH_3$ | H | $SCH_2COO$-i-$C_4H_9$ |
| 1-41 | F | Cl | $CH_3$ | $CH_3$ | H | $SCH_2COO$-c-$C_5H_9$ |
| 1-42 | F | Cl | $CH_3$ | $CH_3$ | H | $SCH_2COO$-c-$C_6H_{11}$ |
| 1-43 | F | Cl | $CH_3$ | $CH_3$ | H | $SCH(CH_3)COOH$ |
| 1-44 | F | Cl | $CH_3$ | $CH_3$ | H | $SCH(CH_3)COOCH_3$ |
| 1-45 | F | Cl | $CH_3$ | $CH_3$ | H | $SCH(CH_3)COOC_2H_5$ |
| 1-46 | F | Cl | $CH_3$ | $CH_3$ | H | $SCH(CH_3)COOC_3H_7$ |
| 1-47 | F | Cl | $CH_3$ | $CH_3$ | H | $SCH(CH_3)COOC_4H_9$ |
| 1-48 | F | Cl | $CH_3$ | $CH_3$ | H | $SCH(CH_3)COOC_5H_{11}$ |
| 1-49 | F | Cl | $CH_3$ | $CH_3$ | H | $SCH(CH_3)COO$-i-$C_3H_7$ |
| 1-50 | F | Cl | $CH_3$ | $CH_3$ | H | $SCH(CH_3)COO$-i-$C_4H_9$ |
| 1-51 | F | Cl | $CH_3$ | $CH_3$ | H | $SCH(CH_3)COO$-c-$C_5H_9$ |
| 1-52 | F | Cl | $CH_3$ | $CH_3$ | H | $SCH(CH_3)COO$-c-$C_6H_{11}$ |

TABLE 3

| Compound | X | Y | R | $R^2$ | $R^3$ | B |
|---|---|---|---|---|---|---|
| 1-53 | F | Cl | $CH_3$ | $CH_3$ | H | COOH |
| 1-54 | F | Cl | $CH_3$ | $CH_3$ | H | $COOCH_3$ |

TABLE 3-continued

| Compound | X | Y | R | R² | R³ | B |
|---|---|---|---|---|---|---|
| 1-55 | F | Cl | $CH_3$ | $CH_3$ | H | $COOC_2H_5$ |
| 1-56 | F | Cl | $CH_3$ | $CH_3$ | H | $COOC_3H_7$ |
| 1-57 | F | Cl | $CH_3$ | $CH_3$ | H | $COOC_4H_9$ |
| 1-58 | F | Cl | $CH_3$ | $CH_3$ | H | $COOCH(CH_3)_2$ |
| 1-59 | F | Cl | $CH_3$ | $CH_3$ | H | $CH_2CH_2COOC_2H_5$ |
| 1-60 | F | Cl | $CH_3$ | $CH_3$ | H | $CH_2CHClCOOC_2H_5$ |
| 1-61 | F | Cl | $CH_3$ | H | H | H |
| 1-62 | F | Cl | $CH_3$ | H | H | OH |
| 1-63 | F | Cl | $CH_3$ | H | H | $OCH_3$ |
| 1-64 | F | Cl | $CH_3$ | H | H | $OC_2H_5$ |
| 1-65 | F | Cl | $CH_3$ | H | H | $OCH(CH_3)_2$ |
| 1-66 | F | Cl | $CH_3$ | H | H | $OCH_2CH=CH_2$ |
| 1-67 | F | Cl | $CH_3$ | H | H | $OCH_2C\equiv CH$ |
| 1-68 | F | Cl | $CH_3$ | H | H | $OCH(CH_3)C\equiv CH$ |
| 1-69 | F | Cl | $CH_3$ | H | H | $OCH_2COOH$ |
| 1-70 | F | Cl | $CH_3$ | H | H | $OCH_2COOCH_3$ |
| 1-71 | F | Cl | $CH_3$ | H | H | $OCH_2COOC_2H_5$ |
| 1-72 | F | Cl | $CH_3$ | H | H | $OCH_2COOC_3H_7$ |
| 1-73 | F | Cl | $CH_3$ | H | H | $OCH_2COOC_4H_9$ |
| 1-74 | F | Cl | $CH_3$ | H | H | $OCH_2COOC_5H_{11}$ |
| 1-75 | F | Cl | $CH_3$ | H | H | $OCH_2COO\text{-}i\text{-}C_3H_7$ |
| 1-76 | F | Cl | $CH_3$ | H | H | $OCH_2COO\text{-}i\text{-}C_4H_9$ |
| 1-77 | F | Cl | $CH_3$ | H | H | $OCH_2COO\text{-}c\text{-}C_5H_9$ |
| 1-78 | F | Cl | $CH_3$ | H | H | $OCH_2COO\text{-}c\text{-}C_6H_{11}$ |

TABLE 4

| Compound | X | Y | R | R² | R³ | B |
|---|---|---|---|---|---|---|
| 1-79 | F | Cl | $CH_3$ | H | H | $OCH(CH_3)COOH$ |
| 1-80 | F | Cl | $CH_3$ | H | H | $OCH(CH_3)COOCH_3$ |
| 1-81 | F | Cl | $CH_3$ | H | H | $OCH(CH_3)COOC_2H_5$ |
| 1-82 | F | Cl | $CH_3$ | H | H | $OCH(CH_3)COOC_3H_7$ |
| 1-83 | F | Cl | $CH_3$ | H | H | $OCH(CH_3)COOC_4H_9$ |
| 1-84 | F | Cl | $CH_3$ | H | H | $OCH(CH_3)COOC_5H_{11}$ |
| 1-85 | F | Cl | $CH_3$ | H | H | $OCH(CH_3)COO\text{-}i\text{-}C_3H_7$ |
| 1-86 | F | Cl | $CH_3$ | H | H | $OCH(CH_3)COO\text{-}i\text{-}C_4H_9$ |
| 1-87 | F | Cl | $CH_3$ | H | H | $OCH(CH_3)COO\text{-}c\text{-}C_5H_9$ |
| 1-88 | F | Cl | $CH_3$ | H | H | $OCH(CH_3)COO\text{-}c\text{-}C_6H_{11}$ |
| 1-89 | F | Cl | $CH_3$ | H | H | $O\text{-}c\text{-}C_5H_9$ |
| 1-90 | F | Cl | $CH_3$ | H | H | $O\text{-}c\text{-}C_6H_{11}$ |
| 1-91 | F | Cl | $CH_3$ | H | H | $SCH_2C\equiv CH$ |
| 1-92 | F | Cl | $CH_3$ | H | H | $SCH(CH_3)C\equiv CH$ |
| 1-93 | F | Cl | $CH_3$ | H | H | $SCH_2COOH$ |
| 1-94 | F | Cl | $CH_3$ | H | H | $SCH_2COOCH_3$ |
| 1-95 | F | Cl | $CH_3$ | H | H | $SCH_2COOC_2H_5$ |
| 1-96 | F | Cl | $CH_3$ | H | H | $SCH_2COOC_3H_7$ |
| 1-97 | F | Cl | $CH_3$ | H | H | $SCH_2COOC_4H_9$ |
| 1-98 | F | Cl | $CH_3$ | H | H | $SCH_2COOC_5H_{11}$ |
| 1-99 | F | Cl | $CH_3$ | H | H | $SCH_2COO\text{-}i\text{-}C_3H_7$ |
| 1-100 | F | Cl | $CH_3$ | H | H | $SCH_2COO\text{-}i\text{-}C_4H_9$ |
| 1-101 | F | Cl | $CH_3$ | H | H | $SCH_2COO\text{-}c\text{-}C_5H_9$ |
| 1-102 | F | Cl | $CH_3$ | H | H | $SCH_2COO\text{-}c\text{-}C_6H_{11}$ |
| 1-103 | F | Cl | $CH_3$ | H | H | $SCH(CH_3)COOH$ |
| 1-104 | F | Cl | $CH_3$ | H | H | $SCH(CH_3)COOCH_3$ |

TABLE 5

| Compound | X | Y | R | R² | R³ | B |
|---|---|---|---|---|---|---|
| 1-105 | F | Cl | $CH_3$ | H | H | $SCH(CH_3)COOC_2H_5$ |
| 1-106 | F | Cl | $CH_3$ | H | H | $SCH(CH_3)COOC_3H_7$ |
| 1-107 | F | Cl | $CH_3$ | H | H | $SCH(CH_3)COOC_4H_9$ |
| 1-108 | F | Cl | $CH_3$ | H | H | $SCH(CH_3)COOC_5H_{11}$ |
| 1-109 | F | Cl | $CH_3$ | H | H | $SCH(CH_3)COO\text{-}i\text{-}C_3H_7$ |
| 1-110 | F | Cl | $CH_3$ | H | H | $SCH(CH_3)COO\text{-}i\text{-}C_4H_9$ |
| 1-111 | F | Cl | $CH_3$ | H | H | $SCH(CH_3)COO\text{-}c\text{-}C_5H_9$ |
| 1-112 | F | Cl | $CH_3$ | H | H | $SCH(CH_3)COO\text{-}c\text{-}C_6H_{11}$ |
| 1-113 | F | Cl | $CH_3$ | H | H | COOH |
| 1-114 | F | Cl | $CH_3$ | H | H | $COOCH_3$ |
| 1-115 | F | Cl | $CH_3$ | H | H | $COOC_2H_5$ |
| 1-116 | F | Cl | $CH_3$ | H | H | $COOC_3H_7$ |

TABLE 5-continued

| Compound | X | Y | R | R² | R³ | B |
|---|---|---|---|---|---|---|
| 1-117 | F | Cl | $CH_3$ | H | H | $COOC_4H_9$ |
| 1-118 | F | Cl | $CH_3$ | H | H | $COOCH(CH_3)_2$ |
| 1-119 | F | Cl | $CH_3$ | H | H | $CH_2CH_2COOC_2H_5$ |
| 1-120 | F | Cl | $CH_3$ | H | H | $CH_2CHClCOOC_2H_5$ |
| 1-121 | H | Cl | $CH_3$ | $CH_3$ | H | H |
| 1-122 | H | Cl | $CH_3$ | $CH_3$ | H | OH |
| 1-123 | H | Cl | $CH_3$ | $CH_3$ | H | $OCH_3$ |
| 1-124 | H | Cl | $CH_3$ | $CH_3$ | H | $OC_2H_5$ |
| 1-125 | H | Cl | $CH_3$ | $CH_3$ | H | $OCH(CH_3)_2$ |
| 1-126 | H | Cl | $CH_3$ | $CH_3$ | H | $OCH_2C\equiv CH$ |
| 1-127 | H | Cl | $CH_3$ | $CH_3$ | H | $OCH(CH_3)C\equiv CH$ |
| 1-128 | H | Cl | $CH_3$ | H | H | H |
| 1-129 | H | Cl | $CH_3$ | H | H | OH |
| 1-130 | H | Cl | $CH_3$ | H | H | $OCH_3$ |

TABLE 6

| Compound | X | Y | R | R² | R³ | B |
|---|---|---|---|---|---|---|
| 1-131 | H | Cl | $CH_3$ | H | H | $OC_2H_5$ |
| 1-132 | H | Cl | $CH_3$ | H | H | $OCH(CH_3)_2$ |
| 1-133 | H | Cl | $CH_3$ | H | H | $OCH_2C\equiv CH$ |
| 1-134 | H | Cl | $CH_3$ | H | H | $OCH(CH_3)C\equiv CH$ |
| 1-135 | Cl | Cl | $CH_3$ | $CH_3$ | H | H |
| 1-136 | Cl | Cl | $CH_3$ | $CH_3$ | H | OH |
| 1-137 | Cl | Cl | $CH_3$ | $CH_3$ | H | $OCH_3$ |
| 1-138 | Cl | Cl | $CH_3$ | $CH_3$ | H | $OC_2H_5$ |
| 1-139 | Cl | Cl | $CH_3$ | $CH_3$ | H | $OCH(CH_3)_2$ |
| 1-140 | Cl | Cl | $CH_3$ | $CH_3$ | H | $OCH_2C\equiv CH$ |
| 1-141 | Cl | Cl | $CH_3$ | $CH_3$ | H | $OCH(CH_3)C\equiv CH$ |
| 1-142 | Cl | Cl | $CH_3$ | H | H | H |
| 1-143 | Cl | Cl | $CH_3$ | H | H | OH |
| 1-144 | Cl | Cl | $CH_3$ | H | H | $OCH_3$ |
| 1-145 | Cl | Cl | $CH_3$ | H | H | $OC_2H_5$ |
| 1-146 | Cl | Cl | $CH_3$ | H | H | $OCH(CH_3)_2$ |
| 1-147 | Cl | Cl | $CH_3$ | H | H | $OCH_2C\equiv CH$ |
| 1-148 | Cl | Cl | $CH_3$ | H | H | $OCH(CH_3)C\equiv CH$ |
| 1-149 | F | Cl | $CH_3$ | $C_2H_5$ | H | H |
| 1-150 | F | Cl | $CH_3$ | $C_2H_5$ | H | OH |
| 1-151 | F | Cl | $CH_3$ | $C_2H_5$ | H | $OCH_3$ |
| 1-152 | F | Cl | $CH_3$ | $C_2H_5$ | H | $OC_2H_5$ |
| 1-153 | F | Cl | $CH_3$ | $C_2H_5$ | H | $OCH(CH_3)_2$ |
| 1-154 | F | Cl | $CH_3$ | $C_2H_5$ | H | $OCH_2C\equiv CH$ |
| 1-155 | F | Cl | $CH_3$ | $C_2H_5$ | H | $OCH(CH_3)C\equiv CH$ |
| 1-156 | F | Cl | $CH_3$ | $C_2H_5$ | H | $OCH_2COOH$ |

TABLE 7

| Compound | X | Y | R | R² | R³ | B |
|---|---|---|---|---|---|---|
| 1-157 | F | Cl | $CH_3$ | $C_2H_5$ | H | $OCH_2COOCH_3$ |
| 1-158 | F | Cl | $CH_3$ | $C_2H_5$ | H | $OCH_2COOC_2H_5$ |
| 1-159 | F | Cl | $CH_3$ | $C_2H_5$ | H | $OCH_2COOC_3H_7$ |
| 1-160 | F | Cl | $CH_3$ | $C_2H_5$ | H | $OCH_2COOC_4H_9$ |
| 1-161 | F | Cl | $CH_3$ | $C_2H_5$ | H | $OCH_2COOC_5H_{11}$ |
| 1-162 | F | Cl | $CH_3$ | $C_2H_5$ | H | $OCH(CH_3)COOH$ |
| 1-163 | F | Cl | $CH_3$ | $C_2H_5$ | H | $OCH(CH_3)COOCH_3$ |
| 1-164 | F | Cl | $CH_3$ | $C_2H_5$ | H | $OCH(CH_3)COOC_2H_5$ |
| 1-165 | F | Cl | $CH_3$ | $C_2H_5$ | H | $OCH(CH_3)COOC_3H_7$ |
| 1-166 | F | Cl | $CH_3$ | $C_2H_5$ | H | $OCH(CH_3)COOC_4H_9$ |
| 1-167 | F | Cl | $CH_3$ | $C_2H_5$ | H | $OCH(CH_3)COOC_5H_{11}$ |
| 1-168 | F | Cl | $CH_3$ | $C_2H_5$ | H | COOH |
| 1-169 | F | Cl | $CH_3$ | $C_2H_5$ | H | $COOCH_3$ |
| 1-170 | F | Cl | $CH_3$ | $C_2H_5$ | H | $COOC_2H_5$ |
| 1-171 | F | Cl | $CH_3$ | $C_2H_5$ | H | $COOC_3H_7$ |
| 1-172 | F | Cl | $CH_3$ | $C_2H_5$ | H | $COOC_4H_9$ |
| 1-173 | F | Cl | $CH_3$ | $C_2H_5$ | H | $COOCH(CH_3)_2$ |
| 1-174 | F | Cl | $CH_3$ | H | $CH_3$ | H |
| 1-175 | F | Cl | $CH_3$ | H | $CH_3$ | OH |
| 1-176 | F | Cl | $CH_3$ | H | $CH_3$ | $OCH_3$ |
| 1-177 | F | Cl | $CH_3$ | H | $CH_3$ | $OC_2H_5$ |
| 1-178 | F | Cl | $CH_3$ | H | $CH_3$ | $OCH(CH_3)_2$ |

TABLE 7-continued

| Compound | X | Y | R | $R^2$ | $R^3$ | B |
|---|---|---|---|---|---|---|
| 1-179 | F | Cl | $CH_3$ | H | $CH_3$ | $OCH_2C\equiv CH$ |
| 1-180 | F | Cl | $CH_3$ | H | $CH_3$ | $OCH(CH_3)C\equiv CH$ |
| 1-181 | F | Cl | $CH_3$ | H | $CH_3$ | $OCH_2COOH$ |
| 1-182 | F | Cl | $CH_3$ | H | $CH_3$ | $OCH_2COOCH_3$ |

TABLE 8

| Compound | X | Y | R | $R^2$ | $R^3$ | B |
|---|---|---|---|---|---|---|
| 1-183 | F | Cl | $CH_3$ | H | $CH_3$ | $OCH_2COOC_2H_5$ |
| 1-184 | F | Cl | $CH_3$ | H | $CH_3$ | $OCH_2COOC_3H_7$ |
| 1-185 | F | Cl | $CH_3$ | H | $CH_3$ | $OCH_2COOC_4H_9$ |
| 1-186 | F | Cl | $CH_3$ | H | $CH_3$ | $OCH_2COOC_5H_{11}$ |
| 1-187 | F | Cl | $CH_3$ | H | $CH_3$ | $OCH(CH_3)COOH$ |
| 1-188 | F | Cl | $CH_3$ | H | $CH_3$ | $OCH(CH_3)COOCH_3$ |
| 1-189 | F | Cl | $CH_3$ | H | $CH_3$ | $OCH(CH_3)COOC_2H_5$ |
| 1-190 | F | Cl | $CH_3$ | H | $CH_3$ | $OCH(CH_3)COOC_3H_7$ |
| 1-191 | F | Cl | $CH_3$ | H | $CH_3$ | $OCH(CH_3)COOC_4H_9$ |
| 1-192 | F | Cl | $CH_3$ | H | $CH_3$ | $OCH(CH_3)COOC_5H_{11}$ |
| 1-193 | F | Cl | $CH_3$ | H | $CH_3$ | $SCH_2COOH$ |
| 1-194 | F | Cl | $CH_3$ | H | $CH_3$ | $SCH_2COOCH_3$ |
| 1-195 | F | Cl | $CH_3$ | H | $CH_3$ | $SCH_2COOC_2H_5$ |
| 1-196 | F | Cl | $CH_3$ | H | $CH_3$ | $SCH_2COOC_3H_7$ |
| 1-197 | F | Cl | $CH_3$ | H | $CH_3$ | $SCH_2COOC_4H_9$ |
| 1-198 | F | Cl | $CH_3$ | H | $CH_3$ | $SCH_2COOC_5H_{11}$ |
| 1-199 | F | Cl | $CH_3$ | H | $CH_3$ | $SCH_2COO\text{-}c\text{-}C_5H_9$ |
| 1-200 | F | Cl | $CH_3$ | H | $CH_3$ | $SCH_2COO\text{-}c\text{-}C_6H_{11}$ |
| 1-201 | F | Cl | $CH_3$ | H | $CH_3$ | $SCH(CH_3)COOH$ |
| 1-202 | F | Cl | $CH_3$ | H | $CH_3$ | $SCH(CH_3)COOCH_3$ |
| 1-203 | F | Cl | $CH_3$ | H | $CH_3$ | $SCH(CH_3)COOC_2H_5$ |
| 1-204 | F | Cl | $CH_3$ | H | $CH_3$ | $SCH(CH_3)COOC_3H_7$ |
| 1-205 | F | Cl | $CH_3$ | H | $CH_3$ | $SCH(CH_3)COOC_4H_9$ |
| 1-206 | F | Cl | $CH_3$ | H | $CH_3$ | $SCH(CH_3)COOC_5H_{11}$ |
| 1-207 | F | Cl | $CH_3$ | H | $CH_3$ | COOH |
| 1-208 | F | Cl | $CH_3$ | H | $CH_3$ | $COOCH_3$ |

TABLE 9

| Compound | X | Y | R | $R^2$ | $R^3$ | B |
|---|---|---|---|---|---|---|
| 1-209 | F | Cl | $CH_3$ | H | $CH_3$ | $COOC_2H_5$ |
| 1-210 | F | Cl | $CH_3$ | H | $CH_3$ | $COOC_3H_7$ |
| 1-211 | F | Cl | $CH_3$ | H | $CH_3$ | $COOC_4H_9$ |
| 1-212 | F | Cl | $CH_3$ | H | $CH_3$ | $COOCH(CH_3)_2$ |
| 1-213 | F | Cl | $C_2H_5$ | $CH_3$ | H | H |
| 1-214 | F | Cl | $C_2H_5$ | $CH_3$ | H | OH |
| 1-215 | F | Cl | $C_2H_5$ | $CH_3$ | H | $OCH_3$ |
| 1-216 | F | Cl | $C_2H_5$ | $CH_3$ | H | $OC_2H_5$ |
| 1-217 | F | Cl | $C_2H_5$ | $CH_3$ | H | $OCH(CH_3)_2$ |
| 1-218 | F | Cl | $C_2H_5$ | $CH_3$ | H | $OCH_2CH=CH_2$ |
| 1-219 | F | Cl | $C_2H_5$ | $CH_3$ | H | $OCH_2C\equiv CH$ |
| 1-220 | F | Cl | $C_2H_5$ | $CH_3$ | H | $OCH(CH_3)C\equiv CH$ |
| 1-221 | F | Cl | $C_2H_5$ | $CH_3$ | H | $OCH_2COOH$ |
| 1-222 | F | Cl | $C_2H_5$ | $CH_3$ | H | $OCH_2COOCH_3$ |
| 1-223 | F | Cl | $C_2H_5$ | $CH_3$ | H | $OCH_2COOC_2H_5$ |
| 1-224 | F | Cl | $C_2H_5$ | $CH_3$ | H | $OCH_2COOC_3H_7$ |
| 1-225 | F | Cl | $C_2H_5$ | $CH_3$ | H | $OCH_2COOC_4H_9$ |
| 1-226 | F | Cl | $C_2H_5$ | $CH_3$ | H | $OCH_2COOC_5H_{11}$ |
| 1-227 | F | Cl | $C_2H_5$ | $CH_3$ | H | $OCH_2COO\text{-}i\text{-}C_3H_7$ |
| 1-228 | F | Cl | $C_2H_5$ | $CH_3$ | H | $OCH_2COO\text{-}i\text{-}C_4H_9$ |
| 1-229 | F | Cl | $C_2H_5$ | $CH_3$ | H | $OCH_2COO\text{-}c\text{-}C_5H_9$ |
| 1-230 | F | Cl | $C_2H_5$ | $CH_3$ | H | $OCH_2COO\text{-}c\text{-}C_6H_{11}$ |
| 1-231 | F | Cl | $C_2H_5$ | $CH_3$ | H | $OCH(CH_3)COOH$ |
| 1-232 | F | Cl | $C_2H_5$ | $CH_3$ | H | $OCH(CH_3)COOCH_3$ |
| 1-233 | F | Cl | $C_2H_5$ | $CH_3$ | H | $OCH(CH_3)COOC_2H_5$ |
| 1-234 | F | Cl | $C_2H_5$ | $CH_3$ | H | $OCH(CH_3)COOC_3H_7$ |

TABLE 10

| Compound | X | Y | R | $R^2$ | $R^3$ | B |
|---|---|---|---|---|---|---|
| 1-235 | F | Cl | $C_2H_5$ | $CH_3$ | H | $OCH(CH_3)COOC_4H_9$ |
| 1-236 | F | Cl | $C_2H_5$ | $CH_3$ | H | $OCH(CH_3)COOC_5H_{11}$ |
| 1-237 | F | Cl | $C_2H_5$ | $CH_3$ | H | $OCH(CH_3)COO\text{-}i\text{-}C_3H_7$ |
| 1-238 | F | Cl | $C_2H_5$ | $CH_3$ | H | $OCH(CH_3)COO\text{-}i\text{-}C_4H_9$ |
| 1-239 | F | Cl | $C_2H_5$ | $CH_3$ | H | $OCH(CH_3)COO\text{-}c\text{-}C_5H_9$ |
| 1-240 | F | Cl | $C_2H_5$ | $CH_3$ | H | $OCH(CH_3)COO\text{-}c\text{-}C_6H_{11}$ |
| 1-241 | F | Cl | $C_2H_5$ | $CH_3$ | H | $O\text{-}c\text{-}C_5H_9$ |
| 1-242 | F | Cl | $C_2H_5$ | $CH_3$ | H | $O\text{-}c\text{-}C_6H_{11}$ |
| 1-243 | F | Cl | $C_2H_5$ | $CH_3$ | H | $SCH_2C\equiv CH$ |
| 1-244 | F | Cl | $C_2H_5$ | $CH_3$ | H | $SCH(CH_3)C\equiv CH$ |
| 1-245 | F | Cl | $C_2H_5$ | $CH_3$ | H | $SCH_2COOH$ |
| 1-246 | F | Cl | $C_2H_5$ | $CH_3$ | H | $SCH_2COOCH_3$ |
| 1-247 | F | Cl | $C_2H_5$ | $CH_3$ | H | $SCH_2COOC_2H_5$ |
| 1-248 | F | Cl | $C_2H_5$ | $CH_3$ | H | $SCH_2COOC_3H_7$ |
| 1-249 | F | Cl | $C_2H_5$ | $CH_3$ | H | $SCH_2COOC_4H_9$ |
| 1-250 | F | Cl | $C_2H_5$ | $CH_3$ | H | $SCH_2COOC_5H_{11}$ |
| 1-251 | F | Cl | $C_2H_5$ | $CH_3$ | H | $SCH_2COO\text{-}i\text{-}C_3H_7$ |
| 1-252 | F | Cl | $C_2H_5$ | $CH_3$ | H | $SCH_2COO\text{-}i\text{-}C_4H_9$ |
| 1-253 | F | Cl | $C_2H_5$ | $CH_3$ | H | $SCH_2COO\text{-}c\text{-}C_5H_9$ |
| 1-254 | F | Cl | $C_2H_5$ | $CH_3$ | H | $SCH_2COO\text{-}c\text{-}C_6H_{11}$ |
| 1-255 | F | Cl | $C_2H_5$ | $CH_3$ | H | $SCH(CH_3)COOH$ |
| 1-256 | F | Cl | $C_2H_5$ | $CH_3$ | H | $SCH_2COOCH_3$ |
| 1-257 | F | Cl | $C_2H_5$ | $CH_3$ | H | $SCH_2COOC_2H_5$ |
| 1-258 | F | Cl | $C_2H_5$ | $CH_3$ | H | $SCH_2COOC_3H_7$ |
| 1-259 | F | Cl | $C_2H_5$ | $CH_3$ | H | $SCH_2COOC_4H_9$ |
| 1-260 | F | Cl | $C_2H_5$ | $CH_3$ | H | $SCH_2COOC_5H_{11}$ |

TABLE 11

| Compound | X | Y | R | $R^2$ | $R^3$ | B |
|---|---|---|---|---|---|---|
| 1-261 | F | Cl | $C_2H_5$ | $CH_3$ | H | $SCH(CH_3)COO\text{-}i\text{-}C_3H_7$ |
| 1-262 | F | Cl | $C_2H_5$ | $CH_3$ | H | $SCH(CH_3)COO\text{-}i\text{-}C_4H_9$ |
| 1-263 | F | Cl | $C_2H_5$ | $CH_3$ | H | $SCH(CH_3)COO\text{-}c\text{-}C_5H_9$ |
| 1-264 | F | Cl | $C_2H_5$ | $CH_3$ | H | $SCH(CH_3)COO\text{-}c\text{-}C_6H_{11}$ |
| 1-265 | F | Cl | $C_2H_5$ | $CH_3$ | H | COOH |
| 1-266 | F | Cl | $C_2H_5$ | $CH_3$ | H | $COOCH_3$ |
| 1-267 | F | Cl | $C_2H_5$ | $CH_3$ | H | $COOC_2H_5$ |
| 1-268 | F | Cl | $C_2H_5$ | $CH_3$ | H | $COOC_3H_7$ |
| 1-269 | F | Cl | $C_2H_5$ | $CH_3$ | H | $COOC_4H_9$ |
| 1-270 | F | Cl | $C_2H_5$ | $CH_3$ | H | $COOCH(CH_3)_2$ |
| 1-271 | F | Cl | $C_2H_5$ | $CH_3$ | H | $CH_2CH_2COOC_2H_5$ |
| 1-272 | F | Cl | $C_2H_5$ | $CH_3$ | H | $CH_2CHClCOOC_2H_5$ |
| 1-273 | F | Cl | $C_2H_5$ | H | H | H |
| 1-274 | F | Cl | $C_2H_5$ | H | H | OH |
| 1-275 | F | Cl | $C_2H_5$ | H | H | $OCH_3$ |
| 1-276 | F | Cl | $C_2H_5$ | H | H | $OC_2H_5$ |
| 1-277 | F | Cl | $C_2H_5$ | H | H | $OCH(CH_3)_2$ |
| 1-278 | F | Cl | $C_2H_5$ | H | H | $OCH_2CH=CH_2$ |
| 1-279 | F | Cl | $C_2H_5$ | H | H | $OCH_2C\equiv CH$ |
| 1-280 | F | Cl | $C_2H_5$ | H | H | $OCH(CH_3)C\equiv CH$ |
| 1-281 | F | Cl | $C_2H_5$ | H | H | $OCH_2COOH$ |
| 1-282 | F | Cl | $C_2H_5$ | H | H | $OCH_2COOCH_3$ |
| 1-283 | F | Cl | $C_2H_5$ | H | H | $OCH_2COOC_2H_5$ |
| 1-284 | F | Cl | $C_2H_5$ | H | H | $OCH_2COOC_3H_7$ |
| 1-285 | F | Cl | $C_2H_5$ | H | H | $OCH_2COOC_4H_9$ |
| 1-286 | F | Cl | $C_2H_5$ | H | H | $OCH_2COOC_5H_{11}$ |

TABLE 12

| Compound | X | Y | R | $R^2$ | $R^3$ | B |
|---|---|---|---|---|---|---|
| 1-287 | F | Cl | $C_2H_5$ | H | H | $OCH_2COO\text{-}i\text{-}C_3H_7$ |
| 1-288 | F | Cl | $C_2H_5$ | H | H | $OCH_2COO\text{-}i\text{-}C_4H_9$ |
| 1-289 | F | Cl | $C_2H_5$ | H | H | $OCH_2COO\text{-}c\text{-}C_5H_9$ |
| 1-290 | F | Cl | $C_2H_5$ | H | H | $OCH_2COO\text{-}c\text{-}C_6H_{11}$ |
| 1-291 | F | Cl | $C_2H_5$ | H | H | $OCH(CH_3)COOH$ |
| 1-292 | F | Cl | $C_2H_5$ | H | H | $OCH(CH_3)COOCH_3$ |
| 1-293 | F | Cl | $C_2H_5$ | H | H | $OCH(CH_3)COOC_2H_5$ |
| 1-294 | F | Cl | $C_2H_5$ | H | H | $OCH(CH_3)COOC_3H_7$ |
| 1-295 | F | Cl | $C_2H_5$ | H | H | $OCH(CH_3)COOC_4H_9$ |
| 1-296 | F | Cl | $C_2H_5$ | H | H | $OCH(CH_3)COOC_5H_{11}$ |

TABLE 12-continued

| Compound | X | Y | R | R² | R³ | B |
|---|---|---|---|---|---|---|
| 1-297 | F | Cl | C₂H₅ | H | H | OCH(CH₃)COO-i-C₃H₇ |
| 1-298 | F | Cl | C₂H₅ | H | H | OCH(CH₃)COO-i-C₄H₉ |
| 1-299 | F | Cl | C₂H₅ | H | H | OCH(CH₃)COO-c-C₅H₉ |
| 1-300 | F | Cl | C₂H₅ | H | H | OCH(CH₃)COO-c-C₆H₁₁ |
| 1-301 | F | Cl | C₂H₅ | H | H | O-c-C₅H₉ |
| 1-302 | F | Cl | C₂H₅ | H | H | O-c-C₆H₁₁ |
| 1-303 | F | Cl | C₂H₅ | H | H | SCH₂C≡CH |
| 1-304 | F | Cl | C₂H₅ | H | H | SCH(CH₃)C≡CH |
| 1-305 | F | Cl | C₂H₅ | H | H | SCH₂COOH |
| 1-306 | F | Cl | C₂H₅ | H | H | SCH₂COOCH₃ |
| 1-307 | F | Cl | C₂H₅ | H | H | SCH₂COOC₂H₅ |
| 1-308 | F | Cl | C₂H₅ | H | H | SCH₂COOC₃H₇ |
| 1-309 | F | Cl | C₂H₅ | H | H | SCH₂COOC₄H₉ |
| 1-310 | F | Cl | C₂H₅ | H | H | SCH₂COOC₅H₁₁ |
| 1-311 | F | Cl | C₂H₅ | H | H | SCH₂COO-i-C₃H₇ |
| 1-312 | F | Cl | C₂H₅ | H | H | SCH₂COO-i-C₄H₉ |

TABLE 13

| Compound | X | Y | R | R² | R³ | B |
|---|---|---|---|---|---|---|
| 1-313 | F | Cl | C₂H₅ | H | H | SCH₂COO-c-C₅H₉ |
| 1-314 | F | Cl | C₂H₅ | H | H | SCH₂COO-c-C₆H₁₁ |
| 1-315 | F | Cl | C₂H₅ | H | H | SCH(CH₃)COOH |
| 1-316 | F | Cl | C₂H₅ | H | H | SCH(CH₃)COOCH₃ |
| 1-317 | F | Cl | C₂H₅ | H | H | SCH(CH₃)COOC₂H₅ |
| 1-318 | F | Cl | C₂H₅ | H | H | SCH(CH₃)COOC₃H₇ |
| 1-319 | F | Cl | C₂H₅ | H | H | SCH(CH₃)COOC₄H₉ |
| 1-320 | F | Cl | C₂H₅ | H | H | SCH(CH₃)COOC₅H₁₁ |
| 1-321 | F | Cl | C₂H₅ | H | H | SCH(CH₃)COO-i-C₃H₇ |
| 1-322 | F | Cl | C₂H₅ | H | H | SCH(CH₃)COO-i-C₄H₉ |
| 1-323 | F | Cl | C₂H₅ | H | H | SCH(CH₃)COO-c-C₅H₉ |
| 1-324 | F | Cl | C₂H₅ | H | H | SCH(CH₃)COO-c-C₆H₁₁ |
| 1-325 | F | Cl | C₂H₅ | H | H | COOH |
| 1-326 | F | Cl | C₂H₅ | H | H | COOCH₃ |
| 1-327 | F | Cl | C₂H₅ | H | H | COOC₂H₅ |
| 1-328 | F | Cl | C₂H₅ | H | H | COOC₃H₇ |
| 1-329 | F | Cl | C₂H₅ | H | H | COOC₄H₉ |
| 1-330 | F | Cl | C₂H₅ | H | H | COOCH(CH₃)₂ |
| 1-331 | F | Cl | C₂H₅ | H | H | CH₂CH₂COOC₂H₅ |
| 1-332 | F | Cl | C₂H₅ | H | H | CH₂CHClCOOC₂H₅ |
| 1-333 | H | Cl | C₂H₅ | CH₃ | H | H |
| 1-334 | H | Cl | C₂H₅ | CH₃ | H | OH |
| 1-335 | H | Cl | C₂H₅ | CH₃ | H | OCH₃ |
| 1-336 | H | Cl | C₂H₅ | CH₃ | H | OC₂H₅ |
| 1-337 | H | Cl | C₂H₅ | CH₃ | H | OCH(CH₃)₂ |
| 1-338 | H | Cl | C₂H₅ | CH₃ | H | OCH₂C≡CH |

TABLE 14

| Compound | X | Y | R | R² | R³ | B |
|---|---|---|---|---|---|---|
| 1-339 | H | Cl | C₂H₅ | CH₃ | H | OCH(CH₃)C≡CH |
| 1-340 | H | Cl | C₂H₅ | H | H | H |
| 1-341 | H | Cl | C₂H₅ | H | H | OH |
| 1-342 | H | Cl | C₂H₅ | H | H | OCH₃ |
| 1-343 | H | Cl | C₂H₅ | H | H | OC₂H₅ |
| 1-344 | H | Cl | C₂H₅ | H | H | OCH(CH₃)₂ |
| 1-345 | H | Cl | C₂H₅ | H | H | OCH₂C≡CH |
| 1-346 | H | Cl | C₂H₅ | H | H | OCH(CH₃)C≡CH |
| 1-347 | Cl | Cl | C₂H₅ | CH₃ | H | H |
| 1-348 | Cl | Cl | C₂H₅ | CH₃ | H | OH |
| 1-349 | Cl | Cl | C₂H₅ | CH₃ | H | OCH₃ |
| 1-350 | Cl | Cl | C₂H₅ | CH₃ | H | OC₂H₅ |
| 1-351 | Cl | Cl | C₂H₅ | CH₃ | H | OCH(CH₃)₂ |
| 1-352 | Cl | Cl | C₂H₅ | CH₃ | H | OCH₂C≡CH |
| 1-353 | Cl | Cl | C₂H₅ | CH₃ | H | OCH(CH₃)C≡CH |
| 1-354 | Cl | Cl | C₂H₅ | H | H | H |
| 1-355 | Cl | Cl | C₂H₅ | H | H | OH |
| 1-356 | Cl | Cl | C₂H₅ | H | H | OCH₃ |
| 1-357 | Cl | Cl | C₂H₅ | H | H | OC₂H₅ |
| 1-358 | Cl | Cl | C₂H₅ | H | H | OCH(CH₃)₂ |

TABLE 14-continued

| Compound | X | Y | R | R² | R³ | B |
|---|---|---|---|---|---|---|
| 1-359 | Cl | Cl | C₂H₅ | H | H | OCH₂C≡CH |
| I-360 | Cl | Cl | C₂H₅ | H | H | OCH(CH₃)C≡CH |
| 1-361 | F | Cl | C₂H₅ | C₂H₅ | H | H |
| 1-362 | F | Cl | C₂H₅ | C₂H₅ | H | OH |
| 1-363 | F | Cl | C₂H₅ | C₂H₅ | H | OCH₃ |
| 1-364 | F | Cl | C₂H₅ | C₂H₅ | H | OC₂H₅ |

TABLE 15

| Compound | X | Y | R | R² | R³ | B |
|---|---|---|---|---|---|---|
| 1-365 | F | Cl | C₂H₅ | C₂H₅ | H | OCH(CH₃)₂ |
| 1-366 | F | Cl | C₂H₅ | C₂H₅ | H | OCH₂C≡CH |
| 1-367 | F | Cl | C₂H₅ | C₂H₅ | H | OCH(CH₃)C≡CH |
| 1-368 | F | Cl | C₂H₅ | C₂H₅ | H | OCH₂COOH |
| 1-369 | F | Cl | C₂H₅ | C₂H₅ | H | OCH₂COOCH₃ |
| 1-370 | F | Cl | C₂H₅ | C₂H₅ | H | OCH₂COOC₂H₅ |
| 1-371 | F | Cl | C₂H₅ | C₂H₅ | H | OCH₂COOC₃H₇ |
| 1-372 | F | Cl | C₂H₅ | C₂H₅ | H | OCH₂COOC₄H₉ |
| 1-373 | F | Cl | C₂H₅ | C₂H₅ | H | OCH₂COOC₅H₁₁ |
| 1-374 | F | Cl | C₂H₅ | C₂H₅ | H | OCH(CH₃)COOH |
| 1-375 | F | Cl | C₂H₅ | C₂H₅ | H | OCH(CH₃)COOCH₃ |
| 1-376 | F | Cl | C₂H₅ | C₂H₅ | H | OCH(CH₃)COOC₂H₅ |
| 1-377 | F | Cl | C₂H₅ | C₂H₅ | H | OCH(CH₃)COOC₃H₇ |
| 1-378 | F | Cl | C₂H₅ | C₂H₅ | H | OCH(CH₃)COOC₄H₉ |
| 1-379 | F | Cl | C₂H₅ | C₂H₅ | H | OCH(CH₃)COOC₅H₁₁ |
| 1-380 | F | Cl | C₂H₅ | C₂H₅ | H | COOH |
| 1-381 | F | Cl | C₂H₅ | C₂H₅ | H | COOCH₃ |
| 1-382 | F | Cl | C₂H₅ | C₂H₅ | H | COOC₂H₅ |
| 1-383 | F | Cl | C₂H₅ | C₂H₅ | H | COOC₃H₇ |
| 1-384 | F | Cl | C₂H₅ | C₂H₅ | H | COOC₄H₉ |
| 1-385 | F | Cl | C₂H₅ | C₂H₅ | H | COOCH(CH₃)₂ |
| 1-386 | F | Cl | C₂H₅ | H | CH₃ | H |
| 1-387 | F | Cl | C₂H₅ | H | CH₃ | OH |
| 1-388 | F | Cl | C₂H₅ | H | CH₃ | OCH₃ |
| 1-389 | F | Cl | C₂H₅ | H | CH₃ | OC₂H₅ |
| 1-390 | F | Cl | C₂H₅ | H | CH₃ | OCH(CH₃)₂ |

TABLE 16

| Compound | X | Y | R | R² | R³ | B |
|---|---|---|---|---|---|---|
| 1-365 | F | Cl | C₂H₅ | H | CH₃ | OCH₂C≡CH |
| 1-392 | F | Cl | C₂H₅ | H | CH₃ | OCH(CH₃)C≡CH |
| 1-393 | F | Cl | C₂H₅ | H | CH₃ | OCH₂COOH |
| 1-394 | F | Cl | C₂H₅ | H | CH₃ | OCH₂COOCH₃ |
| 1-395 | F | Cl | C₂H₅ | H | CH₃ | OCH₂COOC₂H₅ |
| 1-396 | F | Cl | C₂H₅ | H | CH₃ | OCH₂COOC₃H₇ |
| 1-397 | F | Cl | C₂H₅ | H | CH₃ | OCH₂COOC₄H₉ |
| 1-398 | F | Cl | C₂H₅ | H | CH₃ | OCH₂COOC₅H₁₁ |
| 1-399 | F | Cl | C₂H₅ | H | CH₃ | OCH(CH₃)COOH |
| 1-400 | F | Cl | C₂H₅ | H | CH₃ | OCH(CH₃)COOCH₃ |
| 1-401 | F | Cl | C₂H₅ | H | CH₃ | OCH(CH₃)COOC₂H₅ |
| 1-402 | F | Cl | C₂H₅ | H | CH₃ | OCH(CH₃)COOC₃H₇ |
| 1-403 | F | Cl | C₂H₅ | H | CH₃ | OCH(CH₃)COOC₄H₉ |
| 1-404 | F | Cl | C₂H₅ | H | CH₃ | OCH(CH₃)COOC₅H₁₁ |
| 1-405 | F | Cl | C₂H₅ | H | CH₃ | SCH₂COOH |
| 1-406 | F | Cl | C₂H₅ | H | CH₃ | SCH₂COOCH₃ |
| 1-407 | F | Cl | C₂H₅ | H | CH₃ | SCH₂COOC₂H₅ |
| 1-408 | F | Cl | C₂H₅ | H | CH₃ | SCH₂COOC₃H₇ |
| 1-409 | F | Cl | C₂H₅ | H | CH₃ | SCH₂COOC₄H₉ |
| 1-410 | F | Cl | C₂H₅ | H | CH₃ | SCH₂COOC₅H₁₁ |
| 1-411 | F | Cl | C₂H₅ | H | CH₃ | SCH₂COO-c-C₅H₉ |
| 1-412 | F | Cl | C₂H₅ | H | CH₃ | SCH₂COO-c-C₆H₁₁ |
| 1-413 | F | Cl | C₂H₅ | H | CH₃ | SCH(CH₃)COOH |
| 1-414 | F | Cl | C₂H₅ | H | CH₃ | SCH(CH₃)COOCH₃ |
| 1-415 | F | Cl | C₂H₅ | H | CH₃ | SCH(CH₃)COOC₂H₅ |
| 1-416 | F | Cl | C₂H₅ | H | CH₃ | SCH(CH₃)COOC₃H₇ |

TABLE 17

| Compound | X | Y | R | $R^2$ | $R^3$ | B |
|---|---|---|---|---|---|---|
| 1-417 | F | Cl | $C_2H_5$ | H | $CH_3$ | $SCH(CH_3)COOC_4H_9$ |
| 1-418 | F | Cl | $C_2H_5$ | H | $CH_3$ | $SCH(CH_3)COOC_5H_{11}$ |
| 1-419 | F | Cl | $C_2H_5$ | H | $CH_3$ | COOH |
| 1-420 | F | Cl | $C_2H_5$ | H | $CH_3$ | $COOCH_3$ |
| 1-421 | F | Cl | $C_2H_5$ | H | $CH_3$ | $COOC_2H_5$ |
| 1-422 | F | Cl | $C_2H_5$ | H | $CH_3$ | $COOC_3H_7$ |
| 1-423 | F | Cl | $C_2H_5$ | H | $CH_3$ | $COOC_4H_9$ |
| 1-424 | F | Cl | $C_2H_5$ | H | $CH_3$ | $COOCH(CH_3)_2$ |
| 1-425 | F | Cl | $C_3H_7$ | H | $CH_3$ | $OCH(CH_3)_2$ |

TABLE 18

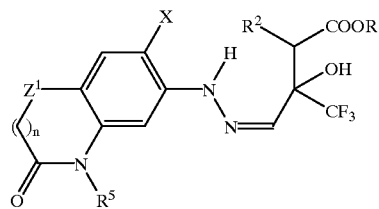

| Compound | X | $Z_1$ | R | n | $R_2$ | $R_5$ |
|---|---|---|---|---|---|---|
| 2-1 | F | O | $CH_3$ | 1 | $CH_3$ | $CH_2C{\equiv}CH$ |
| 2-2 | F | O | $CH_3$ | 1 | $CH_3$ | $CH(CH_3)C{\equiv}CH$ |
| 2-3 | F | O | $CH_3$ | 1 | $CH_3$ | $CH_2COOCH_3$ |
| 2-4 | F | O | $CH_3$ | 1 | $CH_3$ | $CH_2COOC_2H_5$ |
| 2-5 | F | O | $CH_3$ | 1 | $CH_3$ | $CH(CH_3)COOC_2H_5$ |
| 2-6 | F | O | $CH_3$ | 1 | $CH_3$ | $CH_2CN$ |
| 2-7 | F | O | $CH_3$ | 1 | $CH_3$ | $CH(CH_3)_2$ |
| 2-8 | F | O | $CH_3$ | 1 | $CH_3$ | $CH(CH_3)C_2H_5$ |
| 2-9 | F | O | $CH_3$ | 1 | H | $CH_2C{\equiv}CH$ |
| 2-10 | F | O | $CH_3$ | 1 | H | $CH(CH_3)C{\equiv}CH$ |
| 2-11 | F | O | $CH_3$ | 1 | H | $CH_2COOCH_3$ |
| 2-12 | F | O | $CH_3$ | 1 | H | $CH_2COOC_2H_5$ |
| 2-13 | F | O | $CH_3$ | 1 | H | $CH(CH_3)COOC_2H_5$ |
| 2-14 | F | O | $CH_3$ | 1 | H | $CH_2CN$ |
| 2-15 | F | O | $CH_3$ | 1 | H | $CH(CH_3)_2$ |
| 2-16 | F | O | $CH_3$ | 1 | H | $CH(CH_3)C_2H_5$ |
| 2-17 | H | O | $CH_3$ | 1 | $CH_3$ | $CH_2C{\equiv}CH$ |
| 2-18 | H | O | $CH_3$ | 1 | $CH_3$ | $CH(CH_3)C{\equiv}CH$ |
| 2-19 | H | O | $CH_3$ | 1 | $CH_3$ | $CH_2COOCH_3$ |
| 2-20 | H | O | $CH_3$ | 1 | $CH_3$ | $CH_2COOC_2H_5$ |
| 2-21 | H | O | $CH_3$ | 1 | $CH_3$ | $CH(CH_3)COOC_2H_5$ |
| 2-22 | H | O | $CH_3$ | 1 | $CH_3$ | $CH_2CN$ |
| 2-23 | H | O | $CH_3$ | 1 | $CH_3$ | $CH(CH_3)_2$ |
| 2-24 | H | O | $CH_3$ | 1 | $CH_3$ | $CH(CH_3)C_2H_5$ |
| 2-25 | H | O | $CH_3$ | 1 | H | $CH_2C{\equiv}CH$ |
| 2-26 | H | O | $CH_3$ | 1 | H | $CH(CH_3)C{\equiv}CH$ |

TABLE 19

| Compound | X | $Z^1$ | R | n | $R^2$ | $R^5$ |
|---|---|---|---|---|---|---|
| 2-27 | H | O | $CH_3$ | 1 | H | $CH_2COOCH_3$ |
| 2-28 | H | O | $CH_3$ | 1 | H | $CH_2COOC_2H_5$ |
| 2-29 | H | O | $CH_3$ | 1 | H | $CH(CH_3)COOC_2H_5$ |
| 2-30 | H | O | $CH_3$ | 1 | H | $CH_2CN$ |
| 2-31 | H | O | $CH_3$ | 1 | H | $CH(CH_3)_2$ |
| 2-32 | H | O | $CH_3$ | 1 | H | $CH(CH_3)C_2H_5$ |
| 2-33 | F | S | $CH_3$ | 0 | $CH_3$ | $CH_2C{\equiv}CH$ |
| 2-34 | F | S | $CH_3$ | 0 | $CH_3$ | $CH(CH_3)C{\equiv}CH$ |
| 2-35 | F | S | $CH_3$ | 0 | $CH_3$ | $CH_2COOCH_3$ |
| 2-36 | F | S | $CH_3$ | 0 | $CH_3$ | $CH_2COOC_2H_5$ |
| 2-37 | F | S | $CH_3$ | 0 | $CH_3$ | $CH(CH_3)COOC_2H_5$ |
| 2-38 | F | S | $CH_3$ | 0 | $CH_3$ | $CH_2CN$ |
| 2-39 | F | S | $CH_3$ | 0 | $CH_3$ | $CH(CH_3)_2$ |
| 2-40 | F | S | $CH_3$ | 0 | $CH_3$ | $CH(CH_3)C_2H_5$ |
| 2-41 | F | S | $CH_3$ | 0 | H | $CH_2C{\equiv}CH$ |
| 2-42 | F | S | $CH_3$ | 0 | H | $CH(CH_3)C{\equiv}CH$ |
| 2-43 | F | S | $CH_3$ | 0 | H | $CH_2COOCH_3$ |
| 2-44 | F | S | $CH_3$ | 0 | H | $CH_2COOC_2H_5$ |
| 2-45 | F | S | $CH_3$ | 0 | H | $CH(CH_3)COOC_2H_5$ |
| 2-46 | F | S | $CH_3$ | 0 | H | $CH_2CN$ |
| 2-47 | F | S | $CH_3$ | 0 | H | $CH(CH_3)_2$ |
| 2-48 | F | S | $CH_3$ | 0 | H | $CH(CH_3)C_2H_5$ |

TABLE 20

| Compound | X | $Z^1$ | R | n | $R^2$ | $R^5$ |
|---|---|---|---|---|---|---|
| 2-49 | F | O | $C_2H_5$ | 1 | $CH_3$ | $CH_2C{\equiv}CH$ |
| 2-50 | F | O | $C_2H_5$ | 1 | $CH_3$ | $CH(CH_3)C{\equiv}CH$ |
| 2-51 | F | O | $C_2H_5$ | 1 | $CH_3$ | $CH_2COOCH_3$ |
| 2-52 | F | O | $C_2H_5$ | 1 | $CH_3$ | $CH_2COOC_2H_5$ |
| 2-53 | F | O | $C_2H_5$ | 1 | $CH_3$ | $CH(CH_3)COOC_2H_5$ |
| 2-54 | F | O | $C_2H_5$ | 1 | $CH_3$ | $CH_2CN$ |
| 2-55 | F | O | $C_2H_5$ | 1 | $CH_3$ | $CH(CH_3)_2$ |
| 2-56 | F | O | $C_2H_5$ | 1 | $CH_3$ | $CH(CH_3)C_2H_5$ |
| 2-57 | F | O | $C_2H_5$ | 1 | H | $CH_2C{\equiv}CH$ |
| 2-58 | F | O | $C_2H_5$ | 1 | H | $CH(CH_3)C{\equiv}CH$ |
| 2-59 | F | O | $C_2H_5$ | 1 | H | $CH_2COOCH_3$ |
| 2-60 | F | O | $C_2H_5$ | 1 | H | $CH_2COOC_2H_5$ |
| 2-61 | F | O | $C_2H_5$ | 1 | H | $CH(CH_3)COOC_2H_5$ |
| 2-62 | F | O | $C_2H_5$ | 1 | H | $CH_2CN$ |
| 2-63 | F | O | $C_2H_5$ | 1 | H | $CH(CH_3)_2$ |
| 2-64 | F | O | $C_2H_5$ | 1 | H | $CH(CH_3)C_2H_5$ |
| 2-65 | H | O | $C_2H_5$ | 1 | $CH_3$ | $CH_2C{\equiv}CH$ |
| 2-66 | H | O | $C_2H_5$ | 1 | $CH_3$ | $CH(CH_3)C{\equiv}CH$ |
| 2-67 | H | O | $C_2H_5$ | 1 | $CH_3$ | $CH_2COOCH_3$ |
| 2-68 | H | O | $C_2H_5$ | 1 | $CH_3$ | $CH_2COOC_2H_5$ |
| 2-69 | H | O | $C_2H_5$ | 1 | $CH_3$ | $CH(CH_3)COOC_2H_5$ |
| 2-70 | H | O | $C_2H_5$ | 1 | $CH_3$ | $CH_2CN$ |
| 2-71 | H | O | $C_2H_5$ | 1 | $CH_3$ | $CH(CH_3)_2$ |
| 2-72 | H | O | $C_2H_5$ | 1 | $CH_3$ | $CH(CH_3)C_2H_5$ |
| 2-73 | H | O | $C_2H_5$ | 1 | H | $CH_2C{\equiv}CH$ |
| 2-74 | H | O | $C_2H_5$ | 1 | H | $CH(CH_3)C{\equiv}CH$ |

TABLE 21

| Compound | X | $Z^1$ | R | n | $R^2$ | $R^5$ |
|---|---|---|---|---|---|---|
| 2-75 | H | O | $C_2H_5$ | 1 | H | $CH_2COOCH_3$ |
| 2-76 | H | O | $C_2H_5$ | 1 | H | $CH_2COOC_2H_5$ |
| 2-77 | H | O | $C_2H_5$ | 1 | H | $CH(CH_3)COOC_2H_5$ |
| 2-78 | H | O | $C_2H_5$ | 1 | H | $CH_2CN$ |
| 2-79 | H | O | $C_2H_5$ | 1 | H | $CH(CH_3)_2$ |
| 2-80 | H | O | $C_2H_5$ | 1 | H | $CH(CH_3)C_2H_5$ |
| 2-81 | F | S | $C_2H_5$ | 0 | $CH_3$ | $CH_2C{\equiv}CH$ |
| 2-82 | F | S | $C_2H_5$ | 0 | $CH_3$ | $CH(CH_3)C{\equiv}CH$ |
| 2-83 | F | S | $C_2H_5$ | 0 | $CH_3$ | $CH_2COOCH_3$ |
| 2-84 | F | S | $C_2H_5$ | 0 | $CH_3$ | $CH_2COOC_2H_5$ |
| 2-85 | F | S | $C_2H_5$ | 0 | $CH_3$ | $CH(CH_3)COOC_2H_5$ |
| 2-86 | F | S | $C_2H_5$ | 0 | $CH_3$ | $CH_2CN$ |
| 2-87 | F | S | $C_2H_5$ | 0 | $CH_3$ | $CH(CH_3)_2$ |
| 2-88 | F | S | $C_2H_5$ | 0 | $CH_3$ | $CH(CH_3)C_2H_5$ |
| 2-89 | F | S | $C_2H_5$ | 0 | H | $CH_2C{\equiv}CH$ |
| 2-90 | F | S | $C_2H_5$ | 0 | H | $CH(CH_3)C{\equiv}CH$ |
| 2-91 | F | S | $C_2H_5$ | 0 | H | $CH_2COOCH_3$ |
| 2-92 | F | S | $C_2H_5$ | 0 | H | $CH_2COOC_2H_5$ |
| 2-93 | F | S | $C_2H_5$ | 0 | H | $CH(CH_3)COOC_2H_5$ |
| 2-94 | F | S | $C_2H_5$ | 0 | H | $CH_2CN$ |
| 2-95 | F | S | $C_2H_5$ | 0 | H | $CH(CH_3)_2$ |
| 2-96 | F | S | $C_2H_5$ | 0 | H | $CH(CH_3)C_2H_5$ |

Hydrazone compounds of formula (5):

TABLE 22

Q—NH—C(=N-R³)—C(=O)—CF₃ (structure with Q-NH-N=C(R³)-C(O)-CF₃)

| Compound | Q | X | Y | B | R³ |
|---|---|---|---|---|---|
| 3-1 | Q-1 | F | Cl | OH | H |
| 3-2 | Q-1 | F | Cl | H | H |
| 3-3 | Q-1 | F | Cl | OCH(CH₃)₂ | H |
| 3-4 | Q-1 | F | Cl | OCH₂C≡CH | H |
| 3-5 | Q-1 | F | Cl | OCH(CH₃)C≡CH | H |
| 3-6 | Q-1 | F | Cl | OCH₂COOH | H |
| 3-7 | Q-1 | F | Cl | OCH₂COOCH₃ | H |
| 3-8 | Q-1 | F | Cl | OCH₂COOC₂H₅ | H |
| 3-9 | Q-1 | F | Cl | COOCH₃ | H |
| 3-10 | Q-1 | F | Cl | COOC₂H₅ | H |
| 3-11 | Q-1 | H | Cl | H | H |
| 3-12 | Q-1 | H | Cl | OCH(CH₃)₂ | H |
| 3-13 | Q-1 | Cl | Cl | OCH(CH₃)₂ | H |

Malonic acid monoester derivatives of formula (6):

TABLE 23

HOOC—CH(R²)—COOR

| Compound | R | R² |
|---|---|---|
| 4-1 | CH₃ | H |
| 4-2 | C₂H₅ | H |
| 4-3 | CH₃ | CH₃ |
| 4-4 | C₂H₅ | CH₃ |
| 4-5 | CH₃ | C₂H₅ |
| 4-6 | C₂H₅ | C₂H₅ |
| 4-7 | C₃H₇ | CH₃ |

The following illustrates the process for producing pyridazin-3-one derivatives of formula (7) from the present compounds, which process is hereinafter referred to as process 2.

Process 2 can be carried out under the conditions described below. 1) Process 2-1

The present compounds are ring closed in the presence of an organic base such as 1,8-diazabicyclo[5.4.0]undec-7-ene to produce pyridazin-3-one derivatives of formula (7).

The amount of base to be used in the reaction is usually a catalytic amount to a larger excess, preferably 1 mole to an excess, for each one mole of the present compound. The reaction temperature may vary depending upon the base used, and is usually in the range of 30° to 250° C. The reaction time is usually in the range of a moment to 240 hours.

The reaction is usually effected without solvent or in a solvent. Examples of the solvent used in the reaction may include aliphatic hydrocarbons such as hexane, heptane, octane and ligroin; aromatic hydrocarbons such as benzene, toluene, ethylbenzene, xylene and mesitylene; halogenated hydrocarbons such as dichloromethane, chloroform, carbon tetrachloride, 1,2-dichloroethane, chlorobenzene, dichlorobenzene, trichlorobenzene and benzotrifluoride; ethers such as 1,4-dioxane, tetrahydrofuran, ethylene glycol dimethyl ether and methyl t-butyl ether; ketones such as methyl isobutyl ketone and cyclohexanone; acid amides such as N,N-dimethylformamide; and mixtures thereof.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as recrystallization or column chromatography. Thus, the pyridazin-3-one derivatives of formula (7) can be obtained.

2) Process 2-2

The present compounds are ring closed in the presence of a sulfonic acid to produce pyridazin-3-one derivatives of formula (7).

Examples of the sulfonic acid used in the reaction may include p-toluenesulfonic acid and benzenesulfonic acid. The amount of sulfonic acid to be used in the reaction is usually a catalytic amount to a larger excess, preferably 1 mole to an excess, for each one mole of the present compound. The reaction temperature is usually in the range of 30° to 250° C. The reaction time is usually in the range of a moment to 240 hours.

The reaction is usually effected in a solvent. Examples of the solvent used in the reaction may include aliphatic hydrocarbons such as hexane, heptane, octane and ligroin; aromatic hydrocarbons such as benzene, toluene, ethylbenzene, xylene and mesitylene; halogenated hydrocarbons such as dichloromethane, chloroform, carbon tetrachloride, 1,2-dichloroethane, chlorobenzene, dichlorobenzene, trichlorobenzene and benzotrifluoride; ethers such as 1,4-dioxane, tetrahydrofuran, ethylene glycol dimethyl ether and methyl t-butyl ether; ketones such as methyl isobutyl ketone and cyclohexanone; and mixtures thereof.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as recrystallization or column chromatography. Thus, the pyridazin-3-one derivatives of formula (7) can be obtained.

In process 2, depending upon the conditions, the formation of a pyridazin-3-one ring may be accompanied by the replacement of a substituent on the benzene ring.

Some examples of the compounds which can be produced by process 2 are shown in Table 24.

Compounds of formula (15):

TABLE 24

| Compound | X | Y | B | R² | R³ |
|---|---|---|---|---|---|
| 5-1 | F | Cl | OH | CH₃ | H |
| 5-2 | F | Cl | OCH(CH₃)₂ | CH₃ | H |
| 5-3 | F | Cl | OCH₂C≡CH | CH₃ | H |
| 5-4 | F | Cl | OCH(CH₃)C≡CH | CH₃ | H |
| 5-5 | F | Cl | OCH₂COOCH₃ | CH₃ | H |
| 5-6 | F | Cl | OCH₂COOC₂H₅ | CH₃ | H |
| 5-7 | F | Cl | COOCH₃ | CH₃ | H |
| 5-8 | F | Cl | COOC₂H₅ | CH₃ | H |
| 5-9 | F | Cl | OCH(CH₃)₂ | C₂H₅ | H |
| 5-10 | F | Cl | OCH(CH₃)₂ | H | H |

TABLE 24-continued

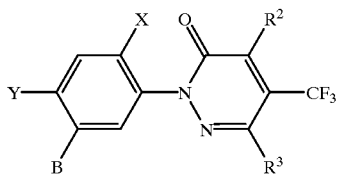

| Compound | X | Y | B | R² | R³ |
|---|---|---|---|---|---|
| 5-11 | F | Cl | OCH₂COOH | CH₃ | H |
| 5-12 | H | Cl | H | CH₃ | H |

The pyridazin-3-one derivatives of formula (7) have excellent herbicidal activity in the foliar and soil treatments on upland fields, for example, against various unfavorable weeds as described below. Polygonaceae:

wild buckwheat (*Polygonum convolvulus*), pale smartweed (*Polygonum lapathiolium*), Pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceae
 common purslane (*Portulaca oleracea*)
Caryophyllaceae
 common chickweed (*Stellaria media*)
Chenopodiaceae
 common lambsquarters (*Chenopodium album*), kochia (*Kochia scoparia*)
Amaranthaceae
 redroot pigweed (*Amaranthus retroflexus*), smooth pigweed (*Amaranthus hybridus*)
Crusiferae
 wild radish (*Raphanus raphanistrum*), wild mustard (*Sinapis arvensis*), shepherdspurse (*Capsella bursa-pastoris*)
Leguminosae
 hemp sesbania (*Sesbania exaltata*), sicklepod (*Cassia obtusifolia*), Florida beggarweed (*Desmodium tortuosum*), white clover (*Trifolium repens*)
Malvaceae
 velvetleaf (*Abutilon theophrasti*), prickly sida (*Sida spinosa*)
Violaceae
 field pansy (*Viola arvensis*), wild pansy (*Viola tricolor*)
Rubiaceae
 catchweed bedstraw (cleavers) (*Galium aparine*)
Convolvulaceae
 ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)
Labiatae
 red deadnettle (*Lamium purpureum*), henbit (*Lamium amplexicaule*)
Solanaceae
 jimsonweed (*Datura stramonium*), black nightshade (*Solanum nigrum*)
Scrophulariaceae
 birdseye speedwell (*Veronica persica*), ivyleaf speedwell (*Veronica hederaefolia*)
Compositae
 common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)
Boraginaceae
 field forget-me-not (*Myosotis arvensis*)
Asclepiadaceae
 common milkweed (*Asclepias syriaca*)
Euphorbiaceae
 sun spurge (*Euphorbia helioscopia*), spotted spurge (*Euphorbia maculata*)
Gramineae
 barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)
Commelinaceae
 common dayflower (*Commelina communis*)
Equisetaceae
 field horsetail (*Equisetum arvense*)
Cyperaceae
 rice flatsedge (*Cyperus iria*), purple nutsedge (*Cyperus rotundus*), yellow nutsedge (*Cyperus esculentus*)

The pyridazin-3-one derivatives of formula (7) can attain effective control of various unfavorable weeds in the no-tillage cultivation of soybean (*Glycine max*), corn (*Zea mays*) and wheat (*Triticum aestivum*).

The pyridazin-3-one derivatives of formula (7) have herbicidal activity in the flooding treatment on paddy fields against various unfavorable weeds as described below.
Gramineae
 barnyardgrass (*Echinochloa oryzicola*)
Scrophulariaceae
 common falsepimpernel (*Lindernia procumbens*)
Lythraceae
 *Rotala indica*, *Ammannia multiflora*
Elatinaceae
 *Elatine triandra*
Cyperaceae
 smallflower umbrellaplant (*Cyperus difformis*), hardstem bulrush (*Scirpus juncoides*), needle spikerush (*Eleocharis acicularis*), *Cyperus serotinus*, *Eleocharis kuroguwai*
Pontederiaceae
 *Monochoria vaginalis*
Alismataceae
 *Sagittaria pygmaea*, *Sagittaria trifolia*, *Alisma canaliculatum*
Potamogetonaceae
 roundleaf pondweed (*Potamogeton distinctus*)
Umbelliferae
 *Oenanthe javanica*

The pyridazin-3-one derivatives of formula (7) can attain effective control of various unfavorable weeds that will grow in orchards, grasslands, lawns, forests, waterways, canals or other non-cultivated lands.

The pyridazin-3-one derivatives of formula (7) have herbicidal activity against various aquatic unfavorable weeds such as water hyacinth (*Eichhornia crassipes*) that will grow in waterways, canals or other watersides.

The pyridazin-3-one derivatives of formula (7) can exhibit selectivity between crop plants and unfavorable weeds for main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (*Gossypium* spp.), sugar beet (*Beta vulgaris*), peanut (*Arachis hypogaea*), sunflower (*Helianthus annuus*) and canola (*Brassica napus*); garden crops such as flowers, ornamental plants and vegetable crops; and transplanted paddy rice.

The pyridazin-3-one derivatives of formula (7) are usually mixed, when used as active ingredients of herbicides, with solid or liquid carriers or diluents, surfactants and other adjuvants to give formulations such as emulsifiable concentrates, wettable powders, flowables, granules, concentrated emulsions or water-dispersible granules.

These formulations contain at least one of the pyridazin-3-one derivatives of formula (7) as an active ingredient at an amount of 0.001% to 80% by weight, preferably 0.005% to 70% by weight, based on the total weight of the formulation.

Examples of the solid carrier or diluent may include fine powders or granules of the following materials: mineral matters such as kaolin clay, attapulgite clay, bentonite, terra alba, pyrophyllite, talc, diatomaceous earth and calcite; organic substances such as walnut shell powder; water-soluble organic substances such as urea; inorganic salts such as ammonium sulfate; and synthetic hydrated silicon oxide. Examples of the liquid carrier or diluent may include aromatic hydrocarbons such as methylnaphthalene, phenylxylylethane, and alkylbenzenes, e.g., xylene; alcohols such as isopropanol, ethylene glycol and 2-ethoxyethanol; esters such as phthalic acid dialkyl esters; ketones such as acetone, cyclohexanone and isophorone; mineral oils such as machine oil; vegetable oils such as soybean oil and cotton seed oil; dimethylsulfoxide, N,N-dimethylformamide, acetonitrile, N-methylpyrrolidone, and water.

Examples of the surfactant used for emulsification, dispersing or spreading may include surfactants of the anionic type, such as alkylsulfates, alkylsulfonates, alkylarylsulfonates, dialkylsulfosuccinates and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters and polyoxyethylene sorbitan fatty acid esters.

Examples of the adjuvant used for formulation may include ligninsulfonates, alginates, polyvinyl alcohol, gum arabic, carboxymethyl cellulose (CMC) and isopropyl acid phosphate (PAP).

The pyridazin-3-one derivatives of formula (7) are usually formulated and used in the soil, foliar or flooding treatment before or after the emergence of unfavorable weeds. The soil treatment may include soil surface treatment and soil incorporation. The foliar treatment may include application over the plants and directed application in which a chemical is applied only to unfavorable weeds so as to keep off the crop plants.

When the pyridazin-3-one derivatives of formula (7) are used as active ingredients of herbicides, the application amount is usually in the range of 0.01 to 10,000 g, preferably 1 to 8000 g, per hectare, although it may vary depending upon the weather conditions, formulation type, application timing, application method, soil conditions, crop plants, unfavorable weeds and other factors. Formulations such as emulsifiable concentrates, wettable powders, flowables, concentrated emulsions or water-dispersible granules are usually applied after diluted at a prescribed amount with about 10 to 1000 liters per hectare of water optionally containing an adjuvant such as a spreading agent. Formulations such as granules or some types of flowables are usually applied without dilution.

Examples of the adjuvant used, if necessary, may include, in addition to the above surfactants, polyoxyethylene resin acids (esters), ligninsulfonates, abietates, dinaphthylmethanedisulfonates, crop oil concentrates, and vegetable oils such as soybean oil, corn oil, cotton seed oil and sunflower oil.

EXAMPLES

The present invention will be further illustrated by the following production examples, formulation examples and test examples; however, the present invention is not limited to these examples.

1) Production of the Present Compounds by Process 1

Production Example 1-1

Under a stream of nitrogen gas, 0.285 g of 3,3,3-trifluoro-2-oxopropanal 1-(4-chloro-2-fluoro-5-isopropoxyphenylhydrazone) was dissolved in 1.7 ml of pyridine at room temperature. To this solution were added 0.086 ml of piperidine and 0.149 g of methylmalonic acid monoethyl ester, and the mixture was heated to 90° C. and stirred for 2 hours. The reaction solution was returned to room temperature and concentrated under reduced pressure. The residue was diluted with 100 ml of diethyl ether. The diluted solution was washed twice with 20 ml of 3 N HCl and once with 30 ml of saturated aqueous sodium bicarbonate solution, dried with magnesium sulfate, filtered, and concentrated under reduced pressure to give a crude product. The crude product was subjected to column chromatography to give 0.224 g of present compound 1-217 as a mixture of the following two isomers.

Isomer 1

$^1$H-NMR (300 MHz, CDCl$_3$, TMS) δ (ppm): 1.25 (t, 3H), 1.31 (d, 3H), 1.37 (d, 3H), 1.38 (d, 3H), 3.24 (q, 1H), 4.16 (q, 2H), 4.49 (m, 1H), 4.68 (s, 1H), 7.02 (d, 1H), 7.05 (d, 1H), 7.48 (brs, 1H), 8.26 (brs, 1H).

Isomer 2

$^1$H-NMR (300 MHz, CDCl$_3$, TMS) δ ppm): 1.26 (t, 3H), 1.36 (d, 9H), 3.20 (q, 1H), 4.20 (m, 2H), 4.47 (m, 1H), 4.84 (s, 1H), 6.98 (d, 1H), 7.04 (d, 1H), 7.20 (brs, 1H), 8.06 (brs, 1H).

Production Example 1-2

First, 5.0 g of 3,3,3-trifluoro-2-oxopropanal 1-(4-chloro-2-fluoro-5-isopropoxyphenylhydrazone) was dissolved in 20 g of toluene. To this solution were added 2.46 g of methylmalonic acid monoethyl ester and 3.1 g of triethylamine, and the mixture was heated under reflux for 8 hours. After completion of the reaction, the reaction solution was returned to room temperature and poured into water, and the mixture was extracted with toluene. The organic layer was washed with diluted hydrochloric acid and then with water, dried, and concentrated. The residue was subjected to column chromatography to give 3.6 g of present compound 1-217.

Production Example 1-3

First, 5.0 g of 3,3,3-trifluoro-2-oxopropanal 1-(4-chloro-2-fluoro-5-isopropoxyphenylhydrazone) was dissolved in 20 g of 1,4-dioxane. To this solution were added 2.46 g of methylmalonic acid monoethyl ester and 2.51 g of sodium acetate, and the mixture was heated under reflux for 24 hours. After completion of the reaction, the reaction solution was returned to room temperature and poured into water, and the mixture was extracted with toluene. The organic layer was washed with diluted hydrochloric acid and then with water, dried, and concentrated. The residue was subjected to column chromatography to give 3.95 g of present compound 1-217.

Production Example 1-4

First, 5.0 g of 3,3,3-trifluoro-2-oxopropanal 1-(4-chloro-2-fluoro-5-isopropoxyphenylhydrazone) was dissolved in 20 g of 1,4-dioxane. To this solution were added 2.46 g of methylmalonic acid monoethyl ester and 4.22 g of potassium carbonate, and the mixture was heated under reflux for 6 hours. After completion of the reaction, the reaction solution was returned to room temperature and poured into water, and the mixture was extracted with toluene. The organic layer was washed with diluted hydrochloric acid and then with water, dried, and concentrated. The residue was subjected to column chromatography to give 1.24 g of present compound 1-217.

2) Production of Pyridazin-3-one Derivatives from the Present Compounds by Process 2

Production Example 2-1

Under a stream of nitrogen gas, 0.224 g of present compound 1-217 was dissolved in 2.0 ml of toluene. To this solution was added 0.189 g of p-toluenesulfonic acid monohydrate, and the mixture was stirred with heating under reflux for 3 hours. The reaction solution was returned to room temperature and diluted with 100 ml of diethyl ether. The diluted solution was washed once with 30 ml of saturated aqueous sodium bicarbonate solution and once with 30 ml of saturated sodium chloride solution, dried with magnesium sulfate, filtered, and concentrated under reduced pressure to give a crude product. The crude product was subjected to column chromatography to give 0.126 g of 2-(2-fluoro-4-chloro-5-isopropoxyphenyl)-4-methyl-5-trifluoromethylpyridazin-3-one, compound 5-2.

$^1$H-NMR (300 MHz, CDCl$_3$, TMS) δ (ppm): 1.38 (d, 6H, J=6.3 Hz), 2.43 (q, 3H, J=2.0 Hz), 4.47 (m, 1H), 6.99 (d, 1H, J=5.0 Hz), 7.29 (d, 1H, J=9.5 Hz), 8.00 (s, 1H).

Production Example 2-2

First, 1.0 g of present compound 1-217 was dissolved in 5.0 g of xylene. To this solution was added 0.35 g of 1,8-diazabicyclo[5.4.0]undec-7-ene, and the reaction was allowed to proceed with heating under reflux for 2 hours. After completion of the reaction, the reaction solution was returned to room temperature and poured into water, and the mixture was extracted with toluene. The organic layer was washed with water, dried, and concentrated. The residue was subjected to column chromatography to give 0.22 g of 2-(2-fluoro-4-chloro-5-isopropoxyphenyl)-4-methyl-5-trifluoromethylpyridazin-3-one, compound 5-2.

The following reference examples illustrate the preparation of starting material compounds used in process 1.

Reference Example 1

To a solution of 5.3 g (53.5 mmol) of sodium acetate dissolved in about 100 ml of water was added 6.6 g (24.3 mmol) of 1,1-dibromo-3,3,3-trifluoroacetone under ice cooling, and the reaction was allowed to proceed at 70° C. for 20 minutes. The reaction solution was left cooling to room temperature, to which a solution of 5.8 g (21.5 mmol) of 2-fluoro-4-chloro-5-isopropoxyphenylhydrazine dissolved in about 20 ml of diethyl ether was added, and the mixture was stirred at room temperature for 1 hour. The organic layer was separated, washed once with 10 ml of saturated aqueous sodium chloride solution, dried with anhydrous magnesium sulfate, and evaporated to remove the diethyl ether. This gave 6.5 g (20.0 mmol) of 3,3,3-trifluoro-2-oxopropanal 1-(4-chloro-2-fluoro-5-isopropoxyphenylhydrazone), compound 3-3.

$^1$H-NMR (250 MHz, CDCl$_3$, TMS) δ (ppm): 1.39 (d, 6H, J=6.0 Hz), 4.38–4.52 (m, 1H), 7.15 (d, 1H, J=10.5 Hz), 7.22 (d, 1H, J=7.3 Hz), 7.43 (q, 1H, J=1.7 Hz), 9.18 (brs, 1H).

Reference Example 2

Production process based on the following scheme:

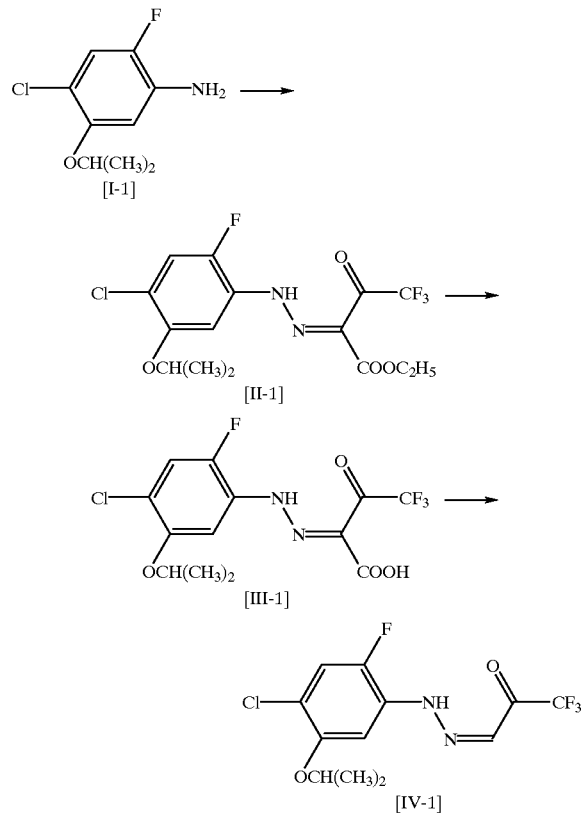

To a solution of 20.1 g of ethyl 4,4,4-trifluoroacetoacetate and 25 g of sodium acetate dissolved in 150 ml of water was added dropwise at a temperature below 10° C. an acid solution of a diazonium salt derived from compound [I-1], which had been prepared from 20.3 g of 4-chloro-2-fluoro-5-isopropoxyaniline, 20 ml of concentrated hydrochloric acid, 20 ml of water, and 7.3 g of sodium nitrite. After completion of the dropwise addition, the mixture was stirred at room temperature for 1 hour, and the resulting crystals were collected by filtration, washed with water, and dried to give 34 g (85% yield) of compound [II-1] in the above scheme as crystals.

To a mixture of 30 ml of 1,4-dioxane and 3 ml of water were added 15.9 g of compound [II-1] obtained by the above reaction and 1.7 g of lithium hydroxide monohydrate, and the mixture was heated under reflux for 6 hours. The reaction solution was poured into ice water, neutralized with diluted hydrochloric acid, and extracted with ethyl acetate. The organic layer was dried and concentrated. The residue was washed with hexane to give 11.3 g (76.3% yield) of compound [III-1].

Then, 7.4 g of compound [III-1] obtained by the above reaction was dissolved in 42 ml of N,N-dimethylformamide. The reaction solution was heated to 100° C., kept at the same temperature for 30 minutes, and then cooled to room temperature. The reaction solution was poured into water and extracted with ethyl acetate. The organic layer was washed with diluted hydrochloric acid, dried with anhydrous magnesium sulfate, and concentrated to give 5.9 g (90% yield) of compound 3-3, compound [IV-1] in the above scheme.

Reference Example 3

Production of malonic acid monoester compound

First, 20.0 g of methylmalonic acid diethyl ester was dissolved in a mixed solution of 30 g of water and 30 g of ethanol. To this solution was added dropwise 9.6 g of 48% aqueous NaOH solution, and the mixture was vigorously stirred at room temperature for 7 hours. After completion of the reaction, the reaction solution was adjusted to pH 3 by the addition of 35% hydrochloric acid and concentrated under reduced pressure. To the residue was added 80 g of water, and the mixture was extracted twice with 40 g of ethyl acetate. The organic layers were combined and concentrated under reduced pressure. To the residue was added 100 g of n-hexane, and the precipitated crystals were collected by filtration. The filtrate was concentrated under reduced pressure to give 16.1 g of methylmalonic acid monoethyl ester.

$^1$H-NMR (250 MHz, CDCl$_3$, TMS) δ (ppm): 1.29 (t, 3H, J=7.1 Hz), 1.44 (d, 3H, J=7.3 Hz), 3.48 (q, 1H, J=7.3 Hz), 4.22 (q, 2H, J=7.1 Hz), 10–13 (brs, 1H).

The following formulation examples illustrate the use of pyridazin-3-one derivatives of formula (7) as active ingredients of herbicides, in which these derivatives are designated by their compound numbers shown in Table 24 above and "parts" is by weight.

Formulation Example 1

Fifty parts of each of compounds 5-1 to 5-9, 3 parts of calcium ligninsulfonate, 2 parts of sodium laurylsulfate, and 45 parts of synthetic hydrated silicon oxide are well pulverized and mixed to give a wettable powder for each compound.

Formulation Example 2

Ten parts of each of compounds 5-1 to 5-9, 14 parts of polyoxyethylene styryl phenyl ether, 6 parts of calcium dodecylbenzenesulfonate, 35 parts of xylene, and 35 parts of cyclohexanone are well mixed to give an emulsifiable concentrate for each compound.

Formulation Example 3

Two parts of each of compounds 5-1 to 5-9, 2 parts of synthetic hydrated silicon oxide, 2 parts of calcium ligninsulfonate, 30 parts of bentonite, and 64 parts of kaolin clay are well pulverized and mixed, to which water is added, and the mixture is well kneaded, granulated, and dried to give a granule for each compound.

Formulation Example 4

Twenty-five parts of each of compounds 5-1 to 5-9, 50 parts of 10% aqueous polyvinyl alcohol solution, and 25 parts of water are mixed and the mixture is pulverized until the mean particle size becomes 5 μm or less to give a flowable for each compound.

The following test examples demonstrate that the pyridazin-3-one derivatives of formula (7) are useful as active ingredients of herbicides.

The herbicidal activity was evaluated at 6 levels with indices of 0 to 5, i.e., designated by numeral "0", "1", "2", "3", "4" or "5", wherein "0" means that no or little difference was observed in the degree of germination or growth between the treated and untreated test plants, i.e., unfavorable weeds and crop plants, at the time of examination and "5" means that the treated test plants died complete or their germination or growth was completely inhibited. The herbicidal activity is excellent when rated at "4" or "5" but insufficient when rated at "3" or lower.

Test Example 1 Foliar Treatment on Upland Fields

Cylindrical plastic pots of 10 cm in diameter and 10 cm in depth were filled with soil. The seeds of entireleaf morningglory (*Ipomoea hederacea* var. *integriuscula*) and velvetleaf (*Abutilon theophrasti*) were sowed in the soil, and the test plants were grown in a greenhouse for 19 days. The test compound was formulated into an emulsifiable concentrate according to Formulation Example 2, which was diluted with water containing a spreading agent to a prescribed concentration. The dilution was uniformly sprayed over the foliage of the test plants with a sprayer at a volume of 1000 liters per hectare. After the application, the test plants were grown in the greenhouse for 19 days, and the herbicidal activity was examined. The results are shown in Table 25.

TABLE 25

| Test compound | Application amount of active ingredient (g/ha) | Herbicidal activity Entireleaf morningglory | Velvetleaf |
|---|---|---|---|
| 5-2 | 500 | 5 | 5 |

Test Example 2 Soil Surface Treatment on Upland Fields

Cylindrical plastic pots of 10 cm in diameter and 10 cm in depth were filled with soil. The seeds of entireleaf morningglory (*Ipomoea hederacea* var. *integriuscula*) and velvetleaf (*Abutilon theophrasti*) were sowed in the soil. The test compound was formulated into an emulsifiable concentrate according to Formulation Example 2, which was diluted with water to a prescribed concentration. The dilution was uniformly sprayed over the soil surface in the pots with a sprayer at a volume of 1000 liters per hectare. After the application, the test plants were grown in a greenhouse for 19 days, and the herbicidal activity was examined. The results are shown in Table 26.

TABLE 26

| Test compound | Application amount of active ingredient (g/ha) | Herbicidal activity Entireleaf morningglory | Velvetleaf |
|---|---|---|---|
| 5-2 | 500 | 5 | 5 |

Test Example 3 Flooding Treatment on Paddy Fields

Cylindrical plastic pots of 9 cm in diameter and 11 cm in depth were filled with soil, in which the seeds of barnyardgrass (*Echinochloa oryzicola*) were sowed. These pots were flooded to form a paddy field, and the test plants were grown in a greenhouse for 7 days. The test compound was formulated into an emulsifiable concentrate according to Formulation Example 2, which was diluted with water to a prescribed concentration. The dilution was applied to the water surface in the pots with a syringe at a volume of 50 liters per are. After the application, the test plants were grown in the greenhouse for 19 days, and the herbicidal activity was examined. The results are shown in Table 27.

TABLE 27

| Test compound | Application amount of active ingredient (g/ha) | Herbicidal activity Barnyardgrass |
|---|---|---|
| 5-2 | 250 | 5 |

Industrial Applicability

The carboxylic acid ester derivatives disclosed herein can be easily converted into pyridazin-3-one derivatives and therefore serve as their important intermediates. The process for producing pyridazin-3-one derivatives from these intermediates in a favorable manner makes a great contribution to the development of pyridazine herbicides with excellent activity.

What is claimed is:

1. A carboxylic acid ester of formula (1):

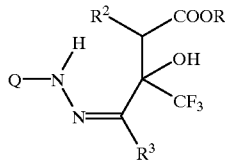

wherein R is $C_1$–$C_6$ alkyl, $R^2$ and $R^3$ are independently hydrogen or $C_1$–$C_3$ alkyl, and Q is Q-1, Q-2, Q-3, Q-4 or Q-5 of formula (2):

Q-1
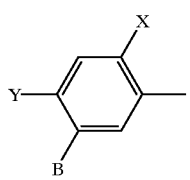

Q-2
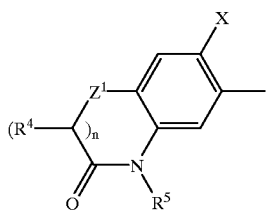

Q-3
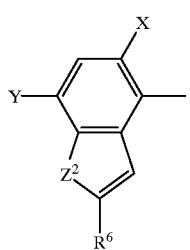

Q-4
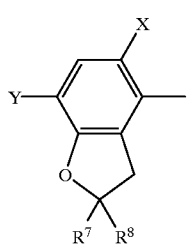

Q-5
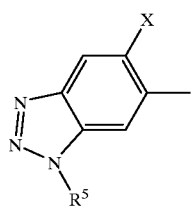

wherein X is hydrogen or halogen;
Y is halogen, nitro, cyano or trifluoromethyl;
$Z^1$ and $Z^2$ are independently oxygen or sulfur;
n is 0 or 1;
$R^4$ is hydrogen or $C_1$–$C_3$ alkyl;

$R^5$ is $C_1$–$C_6$ alkyl, $C_1$–$C_6$ haloalkyl, ($C_3$–$C_6$ cycloalkyl) $C_1$–$C_6$ alkyl, $C_3$–$C_6$ alkenyl, $C_3$–$C_6$ haloalkenyl, $C_3$–$C_6$ alkynyl, $C_3$–$C_6$ haloalkenyl, cyano $C_1$–$C_6$ alkyl, $C_1$–$C_4$ alkoxy $C_1$–$C_4$ alkyl, $C_1$–$C_3$ alkoxy $C_1$–$C_3$ alkoxy $C_1$–$C_3$ alkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy) carbonyl $C_1$–$C_6$ alkyl, —$CH_2CON(R^{12})R^{13}$, —$CH_2COON(R^{12})R^{13}$, —$CH(C_1$–$C_4$ alkyl)CON($R^{12}$) $R^{13}$, —$CH(C_1$–$C_4$ alkyl)COON($R^{12})R^{13}$, $C_1$–$C_4$ alkylthio $C_1$–$C_4$ alkyl or hydroxy $C_1$–$C_6$ alkyl;

$R^{12}$ and $R^{13}$ are independently hydrogen, $C_1$–$C_6$ alkyl, $C_3$–$C_8$ cycloalkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl, ($C_1$–$C_6$ alkyl)carbonyloxy $C_2$–$C_6$ alkyl, ($C_1$–$C_6$ alkyl)carbonylamino $C_2$–$C_6$ alkyl, hydroxy $C_2$–$C_6$ alkyl, benzyl, phenyl or {($C_1$–$C_4$ alkoxy) $C_1$–$C_4$ alkyl}carbonyl $C_1$–$C_6$ alkyl, or $R^{12}$ and $R^{13}$ are taken together to form trimethylene, tetramethylene, pentamethylene, ethyleneoxyethylene or ethylenethio-ethylene;

$R^6$ is $C_1$–$C_6$ alkyl, $C_1$–$C_6$ haloalkyl, cyano, carboxyl, hydroxy $C_1$–$C_6$ alkyl, $C_1$–$C_6$ alkoxy $C_1$–$C_6$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl or ($C_1$–$C_6$ alkoxy)carbonyl;

$R^7$ is hydrogen or $C_1$–$C_6$ alkyl;

$R^8$ is $C_1$–$C_6$ alkyl, $C_1$–$C_6$ haloalkyl, hydroxy $C_1$–$C_6$ alkyl, $C_1$–$C_4$ alkoxy $C_1$–$C_4$ alkyl, $C_1$–$C_3$ alkoxy $C_1$–$C_3$ alkoxy $C_1$–$C_3$ alkyl, ($C_1$–$C_6$ alkyl)carbonyloxy $C_1$–$C_6$ alkyl, ($C_1$–$C_6$ haloalkyl)carbonyl $C_1$–$C_6$ alkyl, carboxyl, carboxy $C_1$–$C_6$ alkyl, ($C_1$–$C_8$ alkoxy) carbonyl, ($C_1$–$C_6$ haloalkoxy)carbonyl, ($C_3$–$C_{10}$ cycloalkoxy)carbonyl, ($C_3$–$C_8$ alkenyloxy)carbonyl, ($C_3$–$C_8$ alkynyloxy)carbonyl, ($C_1$–$C_6$ alkyl) aminocarbonyl, di($C_1$–$C_6$ alkyl)aminocarbonyl, ($C_1$–$C_6$ alkyl)aminocarbonyloxy $C_1$–$C_6$ alkyl or di($C_1$–$C_6$ alkyl)aminocarbonyloxy $C_1$–$C_6$ alkyl;

B is hydrogen, halogen, nitro, cyano, chlorosulfonyl, $OR^1$, $SR^1$, $SO_2OR^{21}$, $COOR^{22}$, $CR^{23}$=$CR^{24}COOR^{25}$ or $CH_2CHWCOOR^{25}$;

W is hydrogen, chlorine or bromine;

$R^1$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkenyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_3$–$C_8$ cycloalkyl) $C_1$–$C_6$ alkoxycarbonyl $C_1$–$C_6$ alkyl, —$CH_2COON(R^{12})R^{13}$, —$CH(C_1$–$C_4$ alkyl)COON ($R^{12})R^{13}$, —$CH_2CON(R^{12})R^{13}$, —$CH(C_1$–$C_4$ alkyl) CON($R^{12})R^{13}$, $C_2$–$C_6$ alkenyloxycarbonyl $C_1$–$C_6$ alkyl, $C_3$–$C_6$ haloalkenyloxycarbonyl $C_1$–$C_6$ alkyl, $C_3$–$C_6$ alkynyloxycarbonyl $C_1$–$C_6$ alkyl, $C_3$–$C_6$ haloalkynyloxycarbonyl $C_1$–$C_6$ alkyl, ($C_1$–$C_6$ alkylthio)carbonyl $C_1$–$C_6$ alkyl, ($C_1$–$C_6$ haloalkylthio) carbonyl $C_1$–$C_6$ alkyl, ($C_3$–$C_6$ alkenylthio)carbonyl $C_1$–$C_6$ alkyl, ($C_3$–$C_6$ haloalkenylthio)carbonyl $C_1$–$C_6$ alkyl, ($C_3$–$C_6$ alkynylthio)carbonyl $C_1$–$C_6$ alkyl, ($C_3$–$C_6$ haloalkynylthio)carbonyl $C_1$–$C_6$ alkyl, ($C_3$–$C_8$ cycloalkylthio)carbonyl $C_1$–$C_6$ alkyl, ($C_3$–$C_8$ cyclohaloalkylthio)carbonyl $C_1$–$C_6$ alkyl, $((C_3$–$C_8$ cycloalkyl) $C_1$–$C_6$ alkylthio)carbonyl $C_1$–$C_6$ alkyl, di($C_1$–$C_6$ alkyl)C=NO carbonyl $C_1$–$C_6$ alkyl, benzylthio)carbonyl $C_1$–$C_6$ alkyl, phenylthio)carbonyl $C_1$–$C_6$ alkyl, hydroxy $C_2$–$C_6$ alkoxycarbonyl $C_1$–$C_6$ alkyl, ($C_1$–$C_6$ alkyl)carbonyloxy $C_2$–$C_6$ alkoxycarbonyl $C_1$–$C_6$ alkyl, ($C_1$–$C_6$ alkyl)carbonylamino $C_2$–$C_6$ alkoxycarbonyl $C_1$–$C_6$ alkyl, {($C_1$–$C_6$ alkoxy)carbonyl $C_1$–$C_6$ alkyl}oxycarbonyl $C_1$–$C_6$ alkyl, hydroxy $C_1$–$C_6$ alkyl, $C_1$–$C_6$ alkoxycarbonyl, $C_1$–$C_6$ haloalkoxycarbonyl, $C_3$–$C_8$ cycloalkoxycarbonyl, $C_3$–$C_6$ alkenyloxycarbonyl, benzyloxycarbonyl, $C_1$–$C_6$ alkylcarbonyl, benzyloxycarbonyl $C_1$–$C_6$ alkyl, phenoxycarbonyl $C_1$–$C_6$ alkyl, furyloxycarbonyl $C_1$–$C_6$ alkyl,furyl $C_1$–$C_6$ alkyloxycarbonyl $C_1$–$C_6$ alkyl, thienyloxycarbonyl $C_1$–$C_6$ alkyl, thienyl $C_1$–$C_6$ alkyloxycarbonyl $C_1$–$C_6$ alkyl, pyrrolyloxycarbonyl $C_1$–$C_6$ alkyl, pyrrolyl $C_1$–$C_6$ alkyloxycarbonyl $C_1$–$C_6$ alkyl, imidazoyloxycarbonyl $C_1$–$C_6$ alkyl, imidazoyl $C_1$–$C_6$ alkyloxycarbonyl $C_1$–$C_6$ alkyl, pyrazoyloxycarbonyl $C_1$–$C_6$ alkyl, pyrazoyl $C_1$–$C_6$ alkyloxycarbonyl $C_1$–$C_6$ alkyl, thiazoyloxycarbonyl $C_1$–$C_6$ alkyl, thiazoyl $C_1$–$C_6$ alkyloxycarbonyl $C_1$–$C_6$ alkyl, oxazoyloxycarbonyl $C_1$–$C_6$ alkyl, oxazoyl $C_1$–$C_6$ alkyloxycarbonyl $C_1$–$C_6$ alkyl, isothiazoyloxycarbonyl $C_1$–$C_6$ alkyl, isothiazoyl $C_1$–$C_6$ alkyloxycarbonyl $C_1$–$C_6$ alkyl, isoxazoyloxycarbonyl $C_1$–$C_6$ alkyl, isoxazoyl $C_1$–$C_6$ alkyloxycarbonyl $C_1$–$C_6$ alkyl, pyridyloxycarbonyl $C_1$–$C_6$ alkyl, pyridyl $C_1$–$C_6$ alkyloxycarbonyl $C_1$–$C_6$ alkyl, pyrazinyloxycarbonyl $C_1$–$C_6$ alkyl, pyrazinyl $C_1$–$C_6$ alkyloxycarbonyl $C_1$–$C_6$ alkyl, pyrimidinyloxycarbonyl $C_1$–$C_6$ alkyl, pyrimidinyl $C_1$–$C_6$ alkyloxycarbonyl $C_1$–$C_6$ alkyl, pyridazinyloxycarbonyl $C_1$–$C_6$ alkyl, pyridazinyl $C_1$–$C_6$ alkyloxycarbonyl $C_1$–$C_6$ alkyl, indolidinyloxycarbonyl $C_1$–$C_6$ alkyl, indolidinyl $C_1$–$C_6$ alkyloxycarbonyl $C_1$–$C_6$ alkyl, indolyloxycarbonyl $C_1$–$C_6$ alkyl, indolyl $C_1$–$C_6$ alkyloxycarbonyl $C_1$–$C_6$ alkyl, indazolyloxycarbonyl $C_1$–$C_6$ alkyl, indazolyl $C_1$–$C_6$ alkyloxycarbonyl $C_1$–$C_6$ alkyl, quinolyloxycarbonyl $C_1$–$C_6$ alkyl, quinolyl $C_1$–$C_6$ alkyloxycarbonyl $C_1$–$C_6$ alkyl, isoquinolyloxycarbonyl $C_1$–$C_6$ alkyl, isoquinolyl $C_1$–$C_6$ alkyloxycarbonyl $C_1$–$C_6$ alkyl, or a group of formula (3):

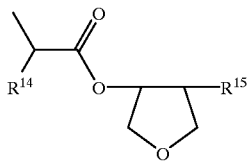

wherein $R^{14}$ is $C_1$–$C_5$ alkyl; $R^{15}$ is hydrogen, hydroxyl or a group of —O—COR$^{16}$; $R^{16}$ is $C_1$–$C_6$ alkyl, $C_1$–$C_6$ haloalkyl, $C_3$–$C_6$ alkenyl, $C_3$–$C_8$ cycloalkyl, phenyl, benzyl or $C_1$–$C_6$ alkoxy, or a group of formula (4):

wherein $R^{17}$ is hydrogen, halogen or $C_1$–$C_6$ alkyl; $R^{18}$ is $C_3$–$C_8$ cycloalkyl, benzyl, $C_2$–$C_{10}$ alkyl with an epoxy group, $C_3$–$C_8$ cycloalkyl $C_1$–$C_6$ alkyl, $C_3$–$C_8$ cycloalkyl $C_2$–$C_6$ alkenyl, $C_1$–$C_6$ alkyl substituted with OR$^{19}$ and OR$^{20}$ on the same carbon atom, $C_2$–$C_6$ alkenyl substituted with OR$^{19}$ and OR$^{20}$ on the same carbon atom, $C_1$–$C_6$ alkyl substituted with SR$^{19}$ and SR$^{20}$ on the same carbon atom, $C_2$–$C_6$ alkenyl substituted with SR$^{19}$ and SR$^{20}$ on the same carbon atom, carboxy $C_2$–$C_6$ alkenyl, ($C_1$–$C_8$ alkoxy)carbonyl $C_2$–$C_6$ alkenyl, ($C_1$–$C_8$ haloalkoxy)carbonyl $C_2$–$C_6$ alkenyl, {($C_1$–$C_4$ alkoxy) $C_2$–$C_4$ alkoxy}carbonyl $C_2$–$C_6$ alkenyl or ($C_3$–$C_8$ cycloalkoxy)carbonyl $C_2$–$C_6$ alkenyl: $R^{19}$ and $R^{20}$ are independently $C_1$–$C_6$ alkyl or $C_1$–$C_6$ haloalkyl, or $R^{19}$ and $R^{20}$ are taken together with to form ethylene optionally substituted with halogen, trimethylene optionally substituted with halogen, tetramethylene optionally substituted with halogen, pentamethylene methylene optionally substituted with halogen, or ethyleneoxyethylene optionally substituted with halogen;

$R^{21}$ is $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkenyl or benzyl;

$R^{22}$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkenyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_1$–$C_6$ alkyl)carbonyl $C_1$–$C_6$ alkyl, ($C_1$–$C_6$ haloalkyl)carbonyl $C_1$–$C_6$ alkyl, {($C_1$–$C_4$ alkoxy) $C_1$–$C_4$ alkyl}carbonyl $C_1$–$C_6$ alkyl, ($C_3$–$C_8$ cycloalkyl)carbonyl $C_1$–$C_6$ alkyl, —CH$_2$COON(R$^{26}$)R$^{27}$, —CH($C_1$–$C_4$ alkyl)COON(R$^{26}$)R$^{27}$, —CH$_2$CON(R$^{26}$)R$^{27}$—CH($C_1$–$C_4$ alkyl)CON(R$^{26}$)R$^{27}$, {($C_1$–$C_6$ alkoxy)carbonyl $C_1$–$C_6$ alkyl}oxycarbonyl $C_1$–$C_6$ alkyl or hydroxy $C_1$–$C_6$ alkyl;

$R^{26}$ and $R^{27}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl or {($C_1$–$C_4$ alkoxy) $C_1$–$C_4$ alkyl}carbonyl $C_1$–$C_6$ alkyl, or $R^{26}$ and $R^{27}$ are taken together to form tetramethylene, pentamethylene or ethyleneoxyethylene;

$R^{23}$ and $R^{24}$ are independently hydrogen, halogen or $C_1$–$C_6$ alkyl; and $R^{25}$ is hydrogen, $C_1$–$C_6$ alkyl, $C_1$–$C_6$ haloalkyl, $C_3$–$C_8$ cycloalkyl or $C_3$–$C_6$ alkenyl.

2. The carboxylic acid ester according to claim 1, wherein Q is Q-1.

3. The carboxylic acid ester according to claim 2, wherein B is hydrogen, OR$^1$ or SR$^1$, and $R^1$ is as defined in claim 1.

4. The carboxylic acid ester according to claim 2, wherein Y is halogen, B is hydrogen, $C_1$–$C_6$ alkoxycarbonyl, OR$^1$ or SR$^1$, and $R^1$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, $C_1$–$C_6$ alkoxycarbonyl, $C_1$–$C_6$ haloalkoxycarbonyl, $C_3$–$C_8$ cycloalkoxycarbonyl, $C_3$–$C_6$ alkenyloxycarbonyl, benzyloxycarbonyl or $C_1$–$C_6$ alkylcarbonyl.

5. The carboxylic acid ester according to claim 2, wherein Y is halogen, B is OR$^1$ or SR$^1$, and $R^1$ is hydrogen or $C_1$–$C_6$ alkyl.

6. The carboxylic acid ester according to claim 4, wherein B is OR$^1$.

7. The carboxylic acid ester according to claim 5, wherein B is OR$^1$.

8. The carboxylic acid ester according to claim 1, wherein R is methyl or ethyl.

9. A process for producing a compound of formula (1), comprising reacting a hydrazone compound of formula (5):

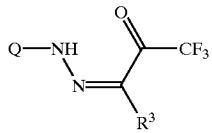

wherein Q and R$^3$ are as defined in claim 1, with a malonic acid monoester derivative of formula (6):

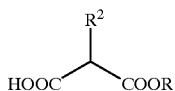

wherein R and R$^2$ are as defined in claim 1, in the presence of a base.

10. The process according to claim 9, wherein the base is sodium acetate, potassium carbonate, 1,8-diazabicyclo[5.4.0]undec-7-ene or triethylamine.

* * * * *